(12) United States Patent
Domkowski et al.

(10) Patent No.: US 7,527,619 B2
(45) Date of Patent: May 5, 2009

(54) MEDICAL FLUID CONTAINER

(75) Inventors: John Domkowski, Kenosha, WI (US);
Richard E. Burg, Libertyville, IL (US);
Glenn A. Caspary, Lake Villa, IL (US);
Marc M. Daniels, Grayslake, IL (US);
Mark I. Ostler, Wadsworth, IL (US);
Joseph Pasini, Libertyville, IL (US);
Stanley F. Pytel, Third Lake, IL (US);
John Sergot, Antioch, IL (US); Sheldon M. Wecker, Libertyville, IL (US)

(73) Assignee: Hospira, Inc., Lake Forest, IL (US)

( * ) Notice: Subject to any disclaimer, the term of this patent is extended or adjusted under 35 U.S.C. 154(b) by 246 days.

(21) Appl. No.: 11/477,061

(22) Filed: Jun. 28, 2006

(65) Prior Publication Data

US 2006/0282061 A1 Dec. 14, 2006

Related U.S. Application Data

(63) Continuation-in-part of application No. 11/315,840, filed on Dec. 21, 2005, which is a continuation-in-part of application No. 11/023,889, filed on Dec. 23, 2004, now Pat. No. 7,488,311.

(51) Int. Cl.
*A61B 19/00* (2006.01)

(52) U.S. Cl. .................. 604/415; 604/408; 604/416; 604/403

(58) Field of Classification Search .............. 604/403, 604/408, 411, 415; 220/62.22; 206/363–366; 383/210.1
See application file for complete search history.

(56) References Cited

U.S. PATENT DOCUMENTS 3,205,889 A   9/1965 Alder et al.
3,364,930 A   1/1968 Ryan
3,547,401 A  12/1970 Beall et al.
4,150,673 A * 4/1979 Watt ........................ 604/408
4,158,362 A   6/1979 Durrett et al.
4,412,573 A  11/1983 Zdeb
4,479,989 A  10/1984 Mahal
4,484,916 A * 11/1984 McPhee ................... 604/256
4,592,092 A   5/1986 McPhee
4,724,028 A   2/1988 Zabielski et al.

(Continued)

FOREIGN PATENT DOCUMENTS

EP      0 373 660       6/1990

(Continued)

OTHER PUBLICATIONS

Unknown author, "Medical/surgical packs make a strong FPA showing," Mar. 1997, Packaging World Magazine, p. 60.

(Continued)

*Primary Examiner*—Leslie R Deak
(74) *Attorney, Agent, or Firm*—Michael R. Crabb

(57) ABSTRACT

A flexible non-PVC, non-DEHP container or bag for medical fluids has a container body formed of a multiple layer polyolefin film. The container has one or more ports equipped with a polyolefin fill tube and port closure assembly. The container has a low moisture vapor transmission rate.

18 Claims, 13 Drawing Sheets

U.S. PATENT DOCUMENTS

| | | | |
|---|---|---|---|
| 4,786,279 A | | 11/1988 | Wilkinson et al. |
| 4,892,222 A | | 1/1990 | Schmidt et al. |
| 4,898,584 A | | 2/1990 | Borsanyi et al. |
| 4,951,845 A | | 8/1990 | Pezzoli et al. |
| 5,088,995 A | | 2/1992 | Packard et al. |
| 5,126,175 A | * | 6/1992 | Yamakoshi ............... 428/35.5 |
| 5,204,305 A | | 4/1993 | Fiasse et al. |
| 5,334,180 A | | 8/1994 | Adolf et al. |
| 5,358,792 A | | 10/1994 | Mehta et al. |
| 5,364,384 A | | 11/1994 | Grabenkort et al. |
| 5,405,333 A | | 4/1995 | Richmond |
| 5,493,845 A | | 2/1996 | Adolf et al. |
| 5,502,112 A | | 3/1996 | Peacock |
| 5,514,123 A | | 5/1996 | Adolf et al. |
| 5,695,840 A | | 12/1997 | Mueller |
| 5,738,663 A | | 4/1998 | Lopez |
| D402,366 S | | 12/1998 | Barney et al. |
| 5,924,584 A | | 7/1999 | Hellstrom et al. |
| 5,925,885 A | | 7/1999 | Clark et al. |
| 5,961,914 A | * | 10/1999 | Mannion et al. ............ 264/544 |
| 6,139,534 A | | 10/2000 | Niedospial, Jr. et al. |
| 6,162,206 A | | 12/2000 | Bindokas et al. |
| 6,179,822 B1 | | 1/2001 | Niedospial, Jr. |
| 6,191,219 B1 | | 2/2001 | Tanaka et al. |
| 6,280,431 B1 | | 8/2001 | Domkowski et al. |
| 6,287,289 B1 | * | 9/2001 | Niedospial, Jr. ............. 604/408 |
| 6,399,704 B1 | | 6/2002 | Laurin et al. |
| 6,425,414 B2 | | 7/2002 | Jorgensen et al. |
| 6,468,377 B1 | | 10/2002 | Sperko et al. |
| 6,723,076 B1 | | 4/2004 | Strobel |
| 6,803,415 B1 | | 10/2004 | Mikielski et al. |
| 7,025,754 B2 | * | 4/2006 | Proicou et al. ............. 604/408 |
| 7,264,608 B2 | * | 9/2007 | Bischof et al. ............ 604/96.01 |
| 2003/0080140 A1 | | 5/2003 | Neas et al. |

FOREIGN PATENT DOCUMENTS

| | | |
|---|---|---|
| EP | 0 416 379 | 3/1991 |
| EP | 0 704 462 | 4/1996 |
| EP | 0 766 955 | 11/2000 |
| JP | 626563 | 4/1994 |
| JP | 2675049 | 7/1997 |
| WO | 98/54260 | 12/1998 |

OTHER PUBLICATIONS

Products webpage for MacoPharma www.macopharma.com dated Dec. 17, 2007.
Unknown Author, "CRYOVAC® M312 Sterilizable Medical Film Is The Next Generation Container For Pharmaceutical Solutions", Press Release by Sealed Air, Mar. 15, 2001.
Hospira, Inc. Material Specification Document No. 10.89-7071 dated Apr. 23, 1999.
Hospira, Inc. Material Specification Document No. 10.89-7072 dated Apr. 23, 1999.
Inoue, Fujio, "A New Package For A Kit Product: A Multiple Chamber Plastic Bag Packaging Parenteral Powder Drug And Diluent", PDA Asian Symposium & Exhibit, Tokyo '94.
McGraw, Inc., Discussion Guide, (Duplex™ Focus Groups) Oct. 24, 1994 (3 pages).
Engineering Drawing No. S6272, entitle "Duplex Container, Oct. 1994".
B. Braun Medical Inc., Brochure, © 2003 B. Braun Medical Inc. Y07-530-307 (Sep. 2003).
B. Braun website: www.bbraunusa.com, "IV Solutions" on Mar. 4, 2004.

* cited by examiner

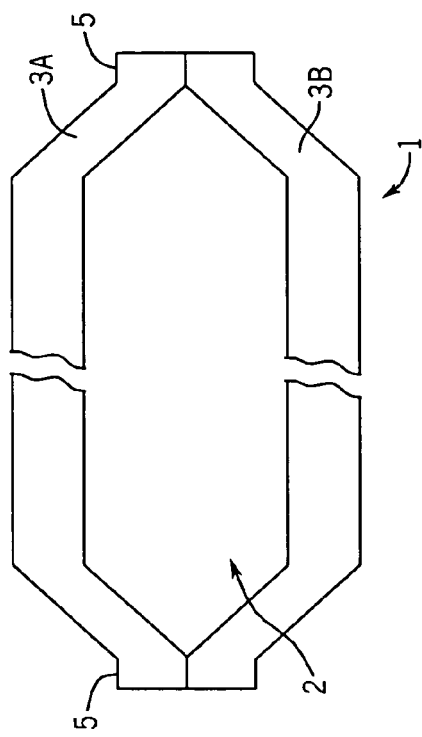
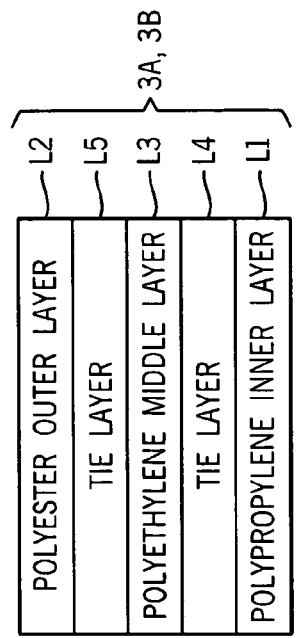
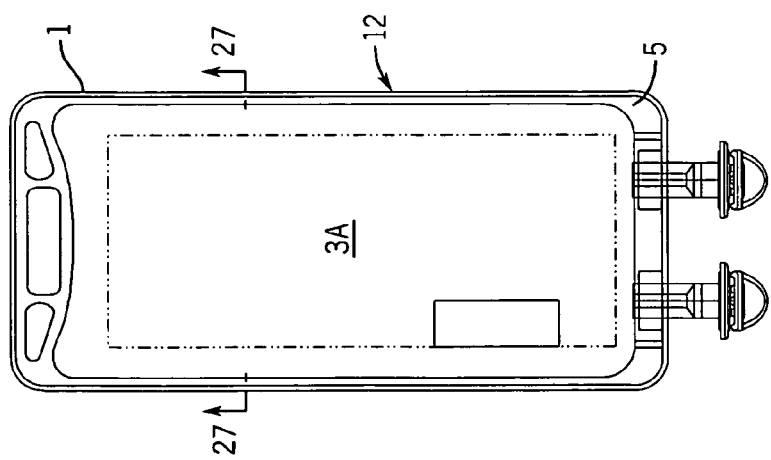
FIG. 27
FIG. 28
FIG. 25

MEDICAL FLUID CONTAINER

CROSS-REFERENCE TO RELATED APPLICATION(S)

This application is a continuation-in-part of U.S. Ser. No. 11/315,840, which was filed Dec. 21, 2005 and was a continuation-in-part of U.S. Ser. No. 11/023,889, which was filed Dec. 23, 2004 now U.S. Pat. No. 7,488,311. The disclosures of those applications are expressly incorporated in their entirety herein.

BACKGROUND OF THE INVENTION

The present invention relates to the field of containers for holding medical fluids for administration to patients. As used herein the term "medical fluids" includes medical, biological and veterinary fluids. Thus the "patients" could be humans, fish, animals, reptiles, amphibians, birds, etc. More particularly, the present invention relates to flexible autoclavable intravenous (IV) fluid containers or bags and non-PVC polyolefin film for their construction. The invention provides long shelf life flexible IV fluid containers that have a low moisture vapor transmission rate and can be terminally sterilized using high temperature treatment, i.e., sterilized after filling to deactivate microorganisms inside the containers (e.g., autoclaving).

Over thirty years ago, the introduction of a flexible IV container raised the issue of water loss and port closure system integrity testing. The selection of a flexible container material system and suitable port closures had to be designed. The most common design selected was some sort of PVC mono-layer film container with a very low cost closure system. Placing another material with higher barrier properties as an overwrap around the filled container solved the issue of the water loss during shelf life. The entire system would then be steam sterilized and delivered to the customer for use.

Polyvinyl Chloride (PVC) is a standard, widely used plastic packaging material used to manufacture flexible containers (bags and pouches) for the administration of small volume parenterals (SVP), often referred to as mini-bags; large volume parenterals (LVP); and various enteral nutritional and liquid preparations. These containers are often utilized for patient hydration and/or to supply pharmaceutical preparations, medicines, vitamins, nutritionals, and the like. Heretofore, PVC has proven to be advantageous because of its resistance to heat, which allows the containers to be terminally sterilized using high temperature treatment.

However, PVC also has its shortcomings. PVC films in the thickness range needed to be acceptably flexible for IV fluid containers typically do not provide a high moisture vapor barrier (MVB). The moisture vapor transmission rate (MVTR) of flexible PVC containers is so high that an overwrap is required to increase the shelf life of the fluids contained therein by providing improved moisture vapor barrier (MVB) properties, as compared to the MVB properties of PVC alone. In other cases, an overwrap is used to contain any leakage and help the port system of the flexible containers to survive autoclaving (i.e., high temperature treatment) or shipping and handling damage. In some cases, and particularly for SVP packages (or bags), multiple SVP packages are placed into one overwrap package. Disadvantageously, once the one overwrap package has been opened, the shelf life of the individual SVP packages contained therein is limited to approximately 30 days, because of the poor MVB properties of PVC. Thus, if a practitioner opens an overwrap containing SVPs, but does not use all of the SVPs in a timely manner, the SVP packages must be discarded approximately 30 days after the overwrap is opened. The overwrap represents added packaging cost and weight, contributes to environmental waste, and depletes petroleum and other resources.

As time passed and new materials and technologies were brought to the pharmaceutical industry, laminated materials typically including three or more layers have come to the forefront for use in IV flexible containers. These laminated materials incorporate an integrated overwrap type film layer to provide the flexible IV container with similar water vapor protection as the separate overwrap system.

To perform well, an intravenous medical fluid container must: 1) drain uniformly, preferably with a readable falling meniscus; 2) have minimal air volume so that patient air embolisms are not an issue; and 3) leave minimal residual volume upon draining so the patient accurately receives the prescribed amount of drug or fluid. Only if the container is flexible, can all of these objectives can be met simultaneously. A flexible container, as the term is used herein, means a container that collapses upon draining, such as a bag for example. Rigid containers, of course, do not change shape substantially upon draining. Semi-rigid containers have substantially the same shape in a filled state and in a drained state, i.e., they may deform some while draining but do not permanently collapse without application of external forces when drained. Semi-rigid containers or plastic bottles also require significant amounts of included air or venting to drain properly. Anyone who has poured milk from a semi-rigid plastic container or oil from a semi-rigid can will appreciate that semi-rigid containers tend to drain sporadically and often unpredictably unless properly vented. Undesirable reversing of flow or suctioning can occur with semi-rigid containers. Heretofore, flexibility has been pursued in conventional intravenous fluid containers by making the material or film of the bag or container very thin (i.e., on the order of a few mils), using a material with a very low modulus of elasticity, or both. However, low modulus or thin films tend to melt at temperatures lower than typical US or European autoclave temperature requirements, and have an undesirably high moisture vapor transmission rate such that an overwrap is required for each container.

Materials other than PVC, such as polyolefins (e.g., polyethylene or polypropylene), nylon, or a composite material, either laminated or co-extruded structure (including both monolayer and multilayer structures), and the like, have been proposed for SVP and/or LVP. One advantage is to reduce or eliminate the use of PVC because of environmental concerns. Another advantage of materials such as polypropylene or polyethylene is that they have better MVB properties than PVC. However, manufacturers and regulatory agencies have been hesitant to eliminate overwraps due to concerns regarding sterility and possible handling damage to and/or leakage from port closure system of polyolefin flexible medical fluid containers. Reliable, economical, longer shelf life, lower moisture vapor transmission rate flexible medical fluid containers have yet to be realized due to port closure deficiencies, the multitude of materials to be selected and/or blended, as well as the many, often conflicting design constraints that must be met. Among these constraints are cold impact strength for "drop tests", capability to withstand the high heat autoclave cycles required in the United States and Europe, USP requirements, drug concentration and assay requirements, allowed fill volume, filling equipment and manufacturing process tolerances, aesthetic appearance (clarity, gloss, haze, wrinkling), printability, drainability, and types and levels of extractables permitted.

Another advantage to replacing PVC with a material such as polypropylene or polyethylene is that products such as pure deionized water (U.S.P. for injection) cannot be effectively packaged in PVC because by-products from the PVC packaging material leach into the pure deionized water, contaminating it, whereas materials such as polyolefins can be formulated so as not to contain by-products that leach into the pure deionized water.

Access ports are commonly used in infusion solution containers to administer solutions to a patient, or to add medicaments or other solutions to the container prior to administration. Current solution containers typically may include a dedicated outlet port for solution administration to a patient and a dedicated inlet port for the addition of diluent or other ingredients to the container.

The outlet port is intended to be coupled to an administrative set and is therefore commonly referred to as the administrative port, whereas the inlet port is designed to permit the injection of therapeutic agents and nutrients into the partially filled container and is sometimes identified as the additive port. Such a container may contain a partial filling of a sterile solution such as saline or dextrose to function as a diluent for the injected additive. Alternatively, the container may house the drug and the diluent can be added by injection into the container through the additive port. The diluted drug or nutrient is then administered to a patient by means of the administrative port and an administrative set that may be either directly or indirectly (i.e., through another solution set) coupled to the patient. Strict limits or tolerances are often imposed on the assay or concentration of the drug to be delivered. Meeting these limits, especially if the filled container is stored for an extended period of time, is difficult if the moisture barrier of the container is too high.

Therefore, an object of this invention is to provide an improved medical fluid container.

A further object of the invention is to provide containers with port closure assemblies that improve the safety and ease of handling when fluids are to be withdrawn or introduced.

Another object of the invention is to provide a port fill tube configuration that increases container sealing reliability, as well as the ease and efficiency of manufacture.

A further object of the invention is to provide a container with container wall formed of a multiple layer polyolefin material selected so as to meet the demanding requirements for terminally sterilized IV containers.

A further object of the invention is to provide an improved method of fabricating and filling medical fluid.

A further object of the invention is to provide an improved method of packaging and storing medical fluid containers.

These and other objects will be apparent to those skilled in the art.

SUMMARY OF THE INVENTION

A container for medical fluids has a container body formed of a multiple layer polyolefin film and includes one or more fluid ports therein. The ports can include a fill tube and a port closure system for association with the fill tube to seal the port closed. The container body, fill tube, and port closure system is free of PVC and DEHP.

A port closure system for use with a fluid container having fluid ports may include administrative and additive port closure assemblies. The administrative port closure assembly receives a piercing pin and includes an administrative housing which seals closed one fluid port. A sleeve extends from an interior surface past a base surface in the administrative housing. The sleeve has an upper portion and a lower portion, of differing diameters. A cap assembly mates with the administrative housing, sealing the interior surface of the administrative housing. A removable cap provides access to the interior surface.

The additive port closure assembly receives a needle and includes a reseal housing which seals closed another fluid port. A cap assembly mates with the reseal housing, sealing an interior face of the reseal housing. As with the administrative port closure assembly, a removable cap provides access to the interior face. A reseal element is mechanically retained, secured or captured between the reseal housing and cap assembly.

The port housings and the fill tubes include various features which facilitate the reliable fabrication and use of the container.

The multiple layer polyolefin film is selected for, among other factors, its impact strength, low moisture vapor transmission rate, its ability to survive autoclaving and heat sealing, and its excellent compatibility with the material of the fill tubes and the port closure assemblies.

DESCRIPTION OF THE DRAWINGS

FIG. 3A is a partial sectional exploded view of the port closure system of the present invention in use with a fluid container.

FIG. 20 is similar to FIG. 19 but shows the same area after the cap assembly is joined to the reseal housing.

FIG. 25 is a top plan view of a container according to one embodiment of the present invention.

FIG. 27 is an enlarged cross-sectional view of the container of the present invention taken along line 27-27 in FIG. 25.

FIG. 28 is a simplified schematic diagram that shows the composition of one embodiment a multilayer polyolefin film which can be used to form the front and back portions of the container wall.

DETAILED DESCRIPTION OF THE EMBODIMENTS OF THE INVENTION

Figure 1:
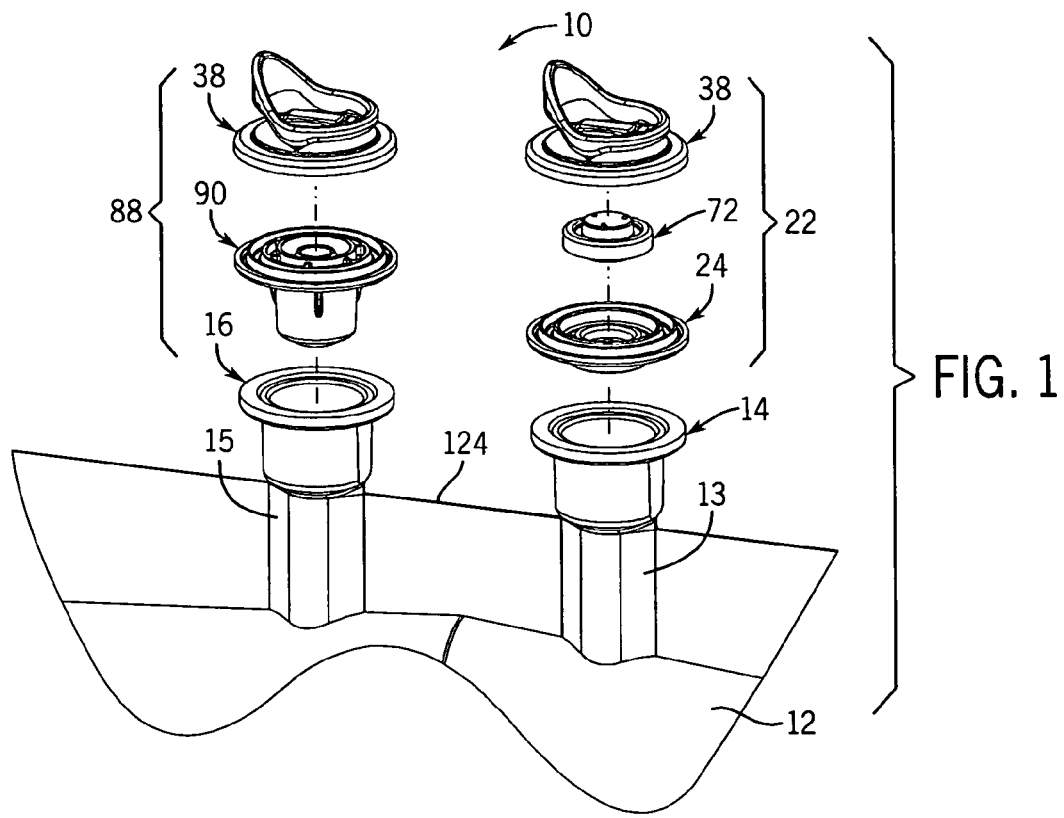
FIG. 1 is a partial exploded perspective view of the port closure system of the present invention in use with a fluid container.
Figure 2:
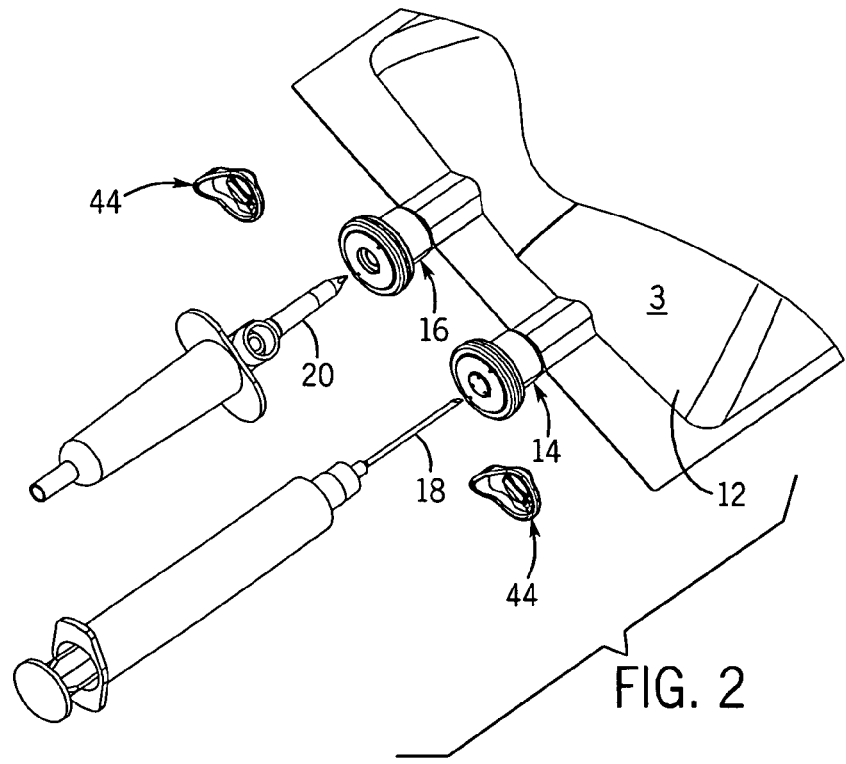
FIG. 2 is a partial perspective view of the port closure system of the present invention in use with a fluid container, needle and piercing pin set.
Figure 3B:
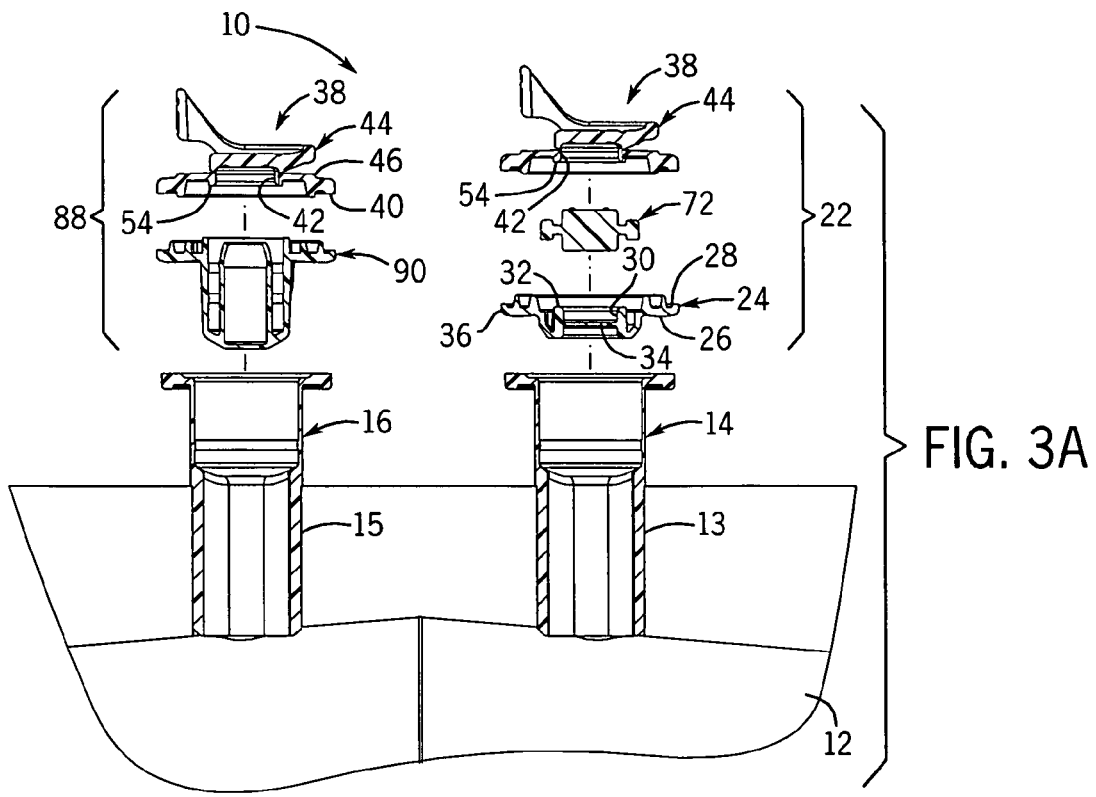
FIG. 3B is a partial sectional assembled view of the port closure system of the present invention in use with a fluid container.
Figure 3B:
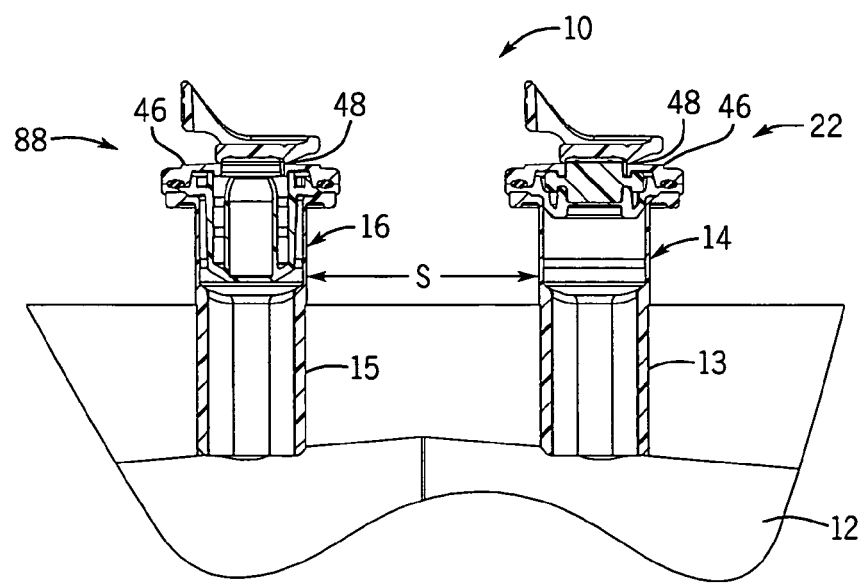

With reference to FIGS. 1-3B, 25, and 27, the flexible long shelf life autoclavable fluid container 12 has a container body 1 with a fluid reservoir 2 formed therein surrounded by a flexible container wall 3. The container wall 3 has a front portion 3A and a back portion 3B. The container body has at least one port 14, 16 formed therein. In one embodiment, such as shown in FIGS. 1-3B, there are two ports 14, 16 located at the same end of the container 12, which has an elongated container body 1.

With reference to FIGS. 1-3B, a port closure system 10 is shown for use with a fluid container 12 which has a flexible container body 1 having at least one port 14, 16 therein. A pair of ports (i.e., two ports) can be provided as first and second fluid ports 14 and 16 accessible respectively with a syringe needle 18 and piercing pin set 20. Fluid ports 14, 16 include fill tubes 13, 15 respectively, which are elongated in one embodiment.

With reference to FIGS. 21-24, the fill tubes 13, 15 can be substantially identical in one embodiment and each have a distal end 17, a proximal end 19 and a fluid passage 21 that extends from the proximal end 19 to the distal end 17. The fill tubes 13, 15 are attached to the container body 1 as described below so that the fluid passage 21 of the fill tube 13, 15 is in fluid communication with the fluid reservoir 2 in the interior of the container body 1. The fill tubes 13, 15 have a generally cylindrical upper portion 23 adjacent to the distal end 17 and a lower portion 25 adjacent to the proximal end 19. The upper portion 23 of the fill tube 13, 15 has a generally cylindrical cavity 27 formed therein for receiving one of the port closure assemblies described in greater detail herein. The upper portion 23 of the fill tube 13, 15 also includes an annular flange 29 that extends radially outward. The flange 29 helps protect the user's fingers from inadvertent contact with a needle, cannula or spike when accessing the ports 14, 16. The upper portion 23 of the fill tube 13, 15 has an outer surface 31 below the flange 29.

The outer surface 31 has at least one notch 33 formed thereon. In one embodiment, the outer surface 31 has a plurality of circumferentially spaced notches 33 formed thereon. In another embodiment, a pair of equally space opposing notches 33 is provided. The notch or notches 33 can be used to orient the fill tube 13, 15 for attachment to the container body 1. The notch or notches 33 can take on many possible configurations and shapes. In one embodiment, the notch 33 has a flat bottom and extends longitudinally along the outer surface 31 of the fill tube 13, 15, it provides a useful place for the user to grasp and hold the fill tube 13, 15.

As best seen in FIGS. 21-24, the lower portion 25 of the elongated fill tube 13, 15 has a non-circular transverse cross-section for a substantial portion of its length. In one embodiment, the non-circular cross-section is rhomboidal or semi-rhomboidal. In another embodiment, the non-circular cross-section is selected from a group of shapes consisting of oval, semi-oval, elliptical, semi-elliptical, rhomboidal and semi-rhomboidal. The non-circular cross-section is defined by a first axis and a second axis transverse to the first axis. The first axis terminates at opposite ends that define the width of the lower portion 25 of the fill tube 13, 15. The second axis terminates at opposite ends that define the depth of the lower portion 25 of the fill tube 13, 15. In one embodiment, the width of the lower portion 25 of the fill tube is greater than the depth, such that the first axis is a major axis and the second axis is a minor axis of the transverse cross-section of the lower portion 25 of the fill tube 13, 15. The notch or notches 33 on the upper portion 23 of the fill tube 13, 15 can be perpendicular to the first or major axis of the lower portion 25, so that automated equipment can easily orient the fill tube 13, 15 properly for attachment to the container body 1 as described below.

The lower portion 25 of the fill tube 13, 15 has an outside radius R1 formed on the opposite ends of the major axis of the transverse cross-section. In one embodiment, the radius R1 is approximately 0.005 to 0.015 inch. In another embodiment, the radius R1 is approximately 0.005 to 0.010 inch. In yet another embodiment, the radius R1 is approximately 0.008 inch. The radius R1 has been found to contribute to the strength and reliability of the fill tube/container body interface or heat seal weld. Improved material flow and fusion at the critical junction Y of the container back, container front and fill tube has been observed with the improved fill tube design.

The lower portion 25 of the fill tube 13, 15 can have an outside radius R2 formed on at least one of the opposite ends of the minor axis of the transverse cross-section. In the embodiment shown in FIG. 22, an outside radius R2 of approximately 1/8 to 1/4 inch is formed on both of the opposite ends of the minor axis. In another embodiment, the radius R2 is approximately 0.150 to 0.200 inch. In yet another embodiment, the radius R2 is approximately 0.178 inches. The radius R2 provides a large, smooth area for heat sealing, adhesion or other attachment means and a light, uniform, unwrinkled stretch of the container body film over the lower portion 25 of the fill tube 13, 15 without over-stretching or over-thinning the container body film material.

Fill tubes 13, 15 having a lower portion 25 with a width of approximately 1/2 inch and a depth of about 1/4 inch have been found to provide acceptable filling and draining characteristics. In one embodiment, the fill tube 13, 15 is about 0.75 to two inches long. In another embodiment, the length of the fill tube 13, 15 is about 1.4 to 1.8 inches. In another embodiment, the fill tube 13, 15 is about 1.5 inches long. The relatively long fill tube lengths help to prevent a standard one inch or 1 1/2 inch long needle, spike or cannula from accidentally penetrating the container wall 3 of the container 12 or IV bag through the passage 21 of the fill tube 13, 15.

The fill tube 13, 15 has a fill tube wall 35 that has sufficient thickness and rigidity to prevent an eighteen gauge needle from being pushed through the wall 35 on a path P that is perpendicular to the wall 35 when a force of three to six lbs. is applied. In one embodiment, the fill tube wall 35 has a substantially uniform thickness of between about 0.9 and 1.5 mm. In another embodiment, the wall 35 is approximately 1.2 mm. The rigidity of the wall 35 is derived from its material, which is described in greater detail below. Table 1 below is a comparison of the force required to puncture the fill tube wall with an eighteen gauge needle perpendicular to the surface for the present invention and commercially available IV bags or flexible containers.

TABLE 1

Needle Puncture Comparison

| Item Tube Specifications | Present Invention | Baxter Viaflex ™ | Braun Excel ™ |
|---|---|---|---|
| General Composition | Rigid | Soft | Soft |
| Wall Thickness (mm) | 1.2 | 0.9 | 1.5 |
| Tube Length (mm) | 39 | 39 | 22 |
| Force to Puncture (lb) | 6.11 | 1.04 | 2.68 |

With reference to FIGS. 1-3B, the ports 14, 16 are connected by a body portion 124 that comprises a flexible web of top and bottom sheets of multilayer film extending transversely across and sealed by heat welding or other means to each other and to the fill tubes 13, 15. With the flexible web 124, the fill tubes 13, 15 of the ports 14, 16 can be independently moved or manipulated. The lower portion 25 of each of the fill tubes 13, 15 is attached to the container body 1 and the fill tubes 13, 15 are spaced apart sufficiently for a user to insert at least one finger therebetween ("fingers" as used herein can include a thumb). With a width of approximately ½ inch for the lower portion 25 of the fill tube 13, 15, a spread S of about one inch can be achieved by placing the centerlines of the tubes 13, 15 of the ports 14, 16 about 1.5 inches apart. The projection of the fill tubes 13, 15 from the container body 1, the location of the flange 29, or the length of the upper portion 23 of the fill tubes 13, 15 can also be selected to provide adequate space for one of the user's fingers.

With reference to FIGS. 2-5, the port closure system 10 includes two port closure assemblies; with the first port assembly being an additive port closure assembly 22 adapted to provide needle 18 sterile access to the first fluid port 14. The additive port closure assembly 22 is adapted to be assembled and sterilized as a subassembly prior to association and use with the fluid container 12.

The additive port closure assembly 22 includes a port housing 24 (hereinafter "reseal housing 24") adapted to seal closed the first fluid port 14 by attachment to the fill tube 13. The reseal housing 24 has a base face 26 adapted to be associated with the first fluid port 14 or fill tube 13 and an interior face 28 adapted to face outwardly from the first fluid port 14. An open cylinder 30 extends from the interior face 28 to the base face 26 and has an upper rim 32. A reseal diaphragm 34 is connected to the open cylinder 30 to seal the open cylinder 30 closed to fluid flow from the container 12. The reseal diaphragm 34 is opened to fluid flow once pierced by needle 18. A reseal flange 36 extends generally radially from the open cylinder 30. The reseal flange 36 protects the user from accidental pricks when applying needle 18 to the additive port closure assembly 22.

The reseal flange 36 and open cylinder 30 are also oriented and arranged to accommodate a commercially available needle-less access system (not shown) being integrated with the reseal housing 24. U.S. Pat. No. 5,924,584 describes one embodiment of a needle-less access system suitable for the present invention; said description is expressly incorporated herein in its entirety.

With reference to FIGS. 3A-6C, a cap assembly 38 of additive port closure assembly 22 is connected to the reseal housing 24. In general, the cap assembly 38 includes an under shell 40 shaped to mate with the interior face 28 of the reseal housing 24. Once mated, the cap assembly 38 seals the interior face 28 from potential contamination. A sealed opening 42 is provided in cap assembly 38, and a removable cap 44 provides access to the sealed opening 42 and the interior face 28. Once the removable cap 44 is detached, the additive port closure assembly 22 need not be re-sterilized, as the cap assembly 38 operates as a sterile barrier to shield the interior face 28 from potential contamination. Removable cap 44 is tamper evident as it cannot be reconnected once removed. Furthermore, if the cap 44 is pierced while still in place, it clearly shows that a hole has been made in the cap (i.e., tampering has taken place).

The cap assembly 38 is of unitary construction and includes a crown 46 connected to the removable cap 44 by an annular frangible area 48. The term "frangible area" as used herein refers to any breakable area or any area with some form of breakable seal.

The crown 46 of the cap assembly 38 has an outer shell 50. The sealed opening 42 extends between the outer and under shells 50 and 40 and provides access to the interior face 28 when the removable cap 44 is detached. A retaining rim 54 extends from the under shell 40 and around the sealed opening 42. A crown flange 56 extends generally radially from the sealed opening 42. The crown flange 56 protects the user from accidental pricks when applying needle 18 to the additive port closure assembly 22.

Figure 6A:
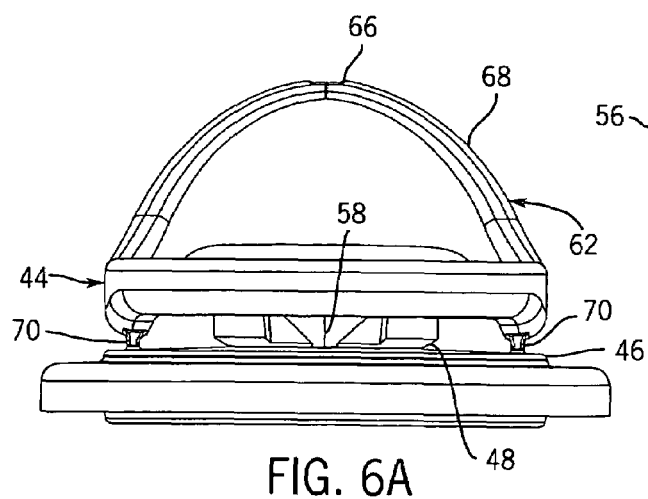
FIG. 6A is a side view of the cap assembly of the present invention.
Figure 6B:
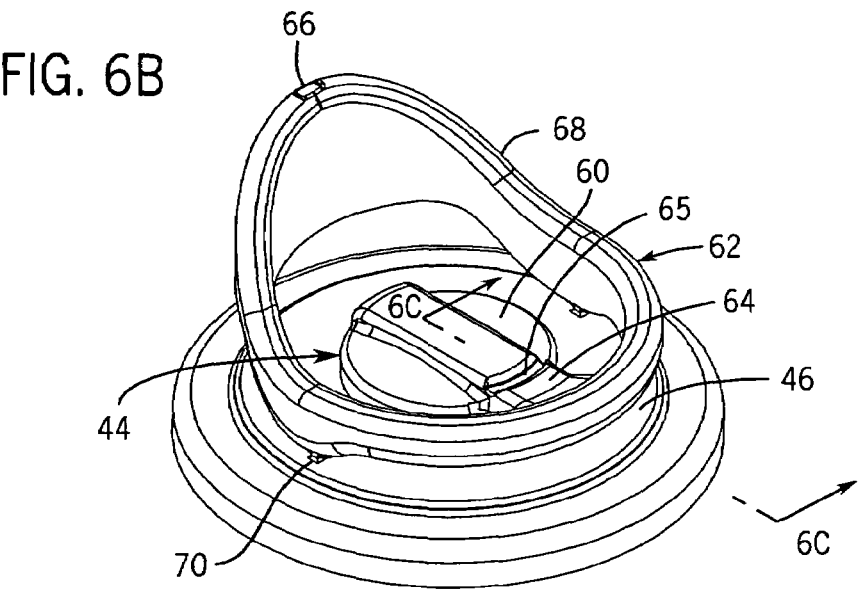
FIG. 6B is a perspective view of the cap assembly of the present invention.
Figure 6C:
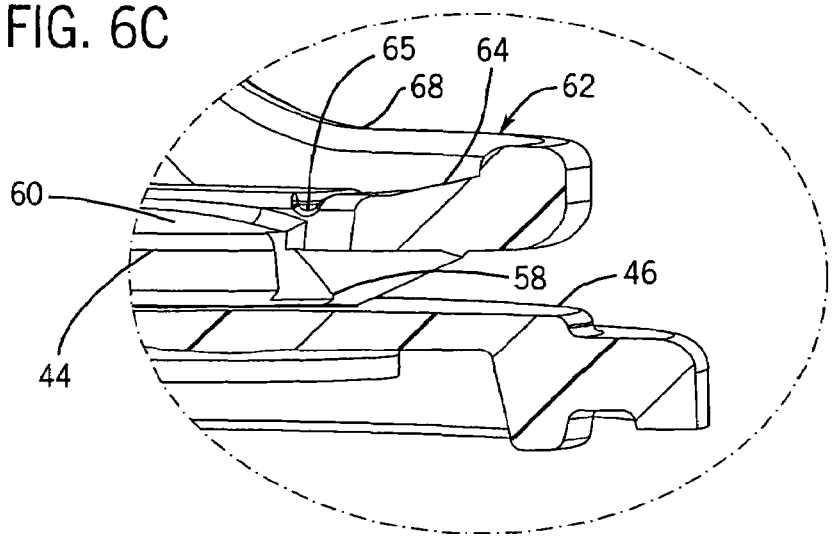
FIG. 6C is an enlarged partial sectional view of the notched portion of the cap assembly taken along line 6C-6C in FIG. 6B.
Figure 7:
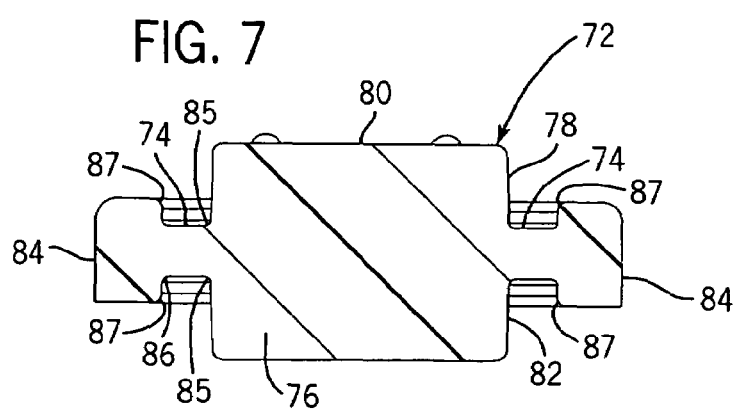
FIG. 7 is a sectional view of the reseal element of the present invention.
Figure 8:
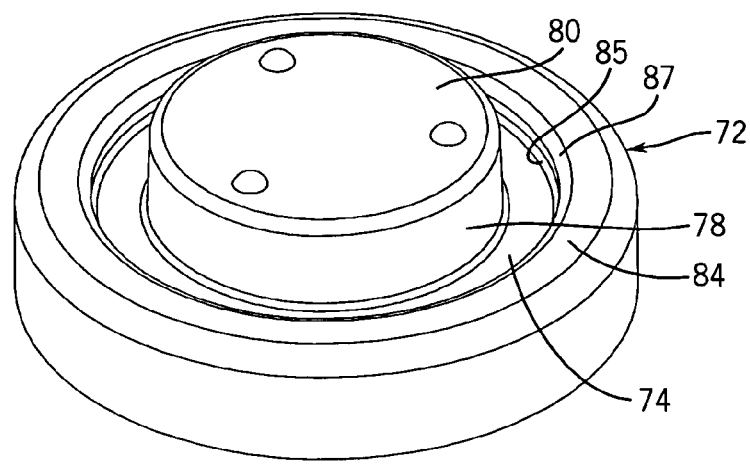
FIG. 8 is a perspective view of the reseal element of the present invention.

A notch area 58 is formed on the cap assembly 38 and is operatively associated with the frangible area 48 to weaken the frangible area 48 near the notch area 58. One skilled in the art will appreciate that the notch area 58 can be on the removable cap 44, as shown in FIG. 6C, or on the crown 46 without detracting from the invention. The notch area 58 can be formed in a variety of force focusing shapes, including but not limited to a partial pyramid shape, a V-shape, or a partial conical shape.

A cover 60 of the removable cap 44 is sealed over the sealed opening 42 by the frangible area 48. The cover 60 has a thickness sufficient to resist manual piercing by needle 18 or piercing pin 20. Due to the melt temperature of the material of the cover 60 being in the range of 129-144° C. and the presence of an air chamber under the cover once assembled, the cover 60 is adapted to shape changes during heat sterilization, which allows a user to discern the sterilized state of the additive port closure assembly 22 due to the shape of cover 60.

A pull element 62 of the removable cap 44 is connected to the cover 60 to allow a user to manually tug on the pull element 62 to sever the frangible area 48 and separate the cover 60 from the crown 46. The pull element 62 includes a lever 64 connected to one side of the cover and adjacent to the crown 46. The lever 64 is positioned adjacent the notch area 58 and focuses the user tugging force on the pull element 62 at the notch area 58. The lever 64 includes an area of narrowed cross section that defines a pull force concentrator. The pull force concentrator is adjacent the frangible area 48 and near the notch area 58. Preferably the pull force concentrator is defined by a transverse groove 65 having rounded side walls in the top of the lever 64, although other shapes, orientations and locations will not detract from the invention so long as the structure focuses or concentrates the user tugging force on the pull element at the notch area 58.

A pull tab 66 is connected to the lever 64 by a pull ring 68 and positioned opposite the lever 64 on the pull ring 68. The pull tab 66 provides an area for a user to manually grip and tug on the pull element 62.

At least one pivot element 70 is radially spaced from the frangible area 48 and circumferentially spaced from the lever 64 on the pull ring 68. More preferably, a pair of pivot elements is positioned so each pivot element is equally spaced about ninety degrees away from the lever 64. The pivot elements 70 contact the crown 46 and pivot to absorb any impact forces on the pull element 62 to prevent inadvertent damage to the frangible area 48. Additional pivot elements may be utilized as needed.

With reference to FIGS. 3A, 4, 5 and 7, a reseal element 72 of the removable cap 44 is positioned between the under shell 40 of the crown 46 and the interior face 28 of the reseal housing 24. The reseal element 72 has an annular shoulder 74 extending radially from a central core 76. The annular shoulder 74 splits the central core 76 into an upper core 78 having a raised surface 80 and a lower core 82.

The raised surface 80 extends beyond the sealed opening 42 in the cap assembly 38 when the removable cap 44 is detached. The exposed raised surface 80 provides a convenient swabbable area to sterilize during subsequent uses.

The lower core 82 is received within the open cylinder 30 of the reseal housing 24. The diameter of the lower core 82 is selected relative to the diameter of the open cylinder 30 such that the open cylinder 30 presses radially inward on the lower core 82 to provide a seal therebetween and to re-seal the reseal element 72 itself when punctured. In other words, the lower core 82 is frictionally fitted or forcibly pressed into the open cylinder 30 of the reseal housing 24. This frictional fit provides one means of securing or retaining the reseal element 72 in the reseal housing 24 for subsequent assembly operations.

An annular lip element 84 is connected to an outer rim 86 of the annular shoulder 74. The junction of the rim 86 and the lip element 84 has a fillet or inside radius 85. The lip element 84 extends transversely to the annular shoulder 74 in two directions. The upper and lower inside edges of the lip element 84 have a chamfer, inside radius or fillet 87 thereon to assist in molding and guide the retaining rim 54 or rim 32 toward the annular shoulder 74. The annular lip element 84 has an inside diameter greater than the outside diameter of the retaining rim 54 and an outside diameter less than the outer diameter of the crown flange 56. The reseal element 72 is mechanically retained, held, secured, or more particularly clamped in place by the retaining rim 54 of the crown 46 and the upper rim 32 of the open cylinder 30, which upon the cap assembly 38 and reseal housing 24 being connected together are received between the central core 76 and the lip element 84 so as to retain the annular shoulder 74. The uncompressed height of the annular shoulder 74 can be selected to be equal to, or more preferably greater than, the distance between the retaining rim 54 and the rim 32 when the cap 44 and reseal housing 24 are joined. Selecting an uncompressed height greater than the available distance provides a desirable clamping force or sealing on the resilient material of the reseal element 72 at the shoulder 74. Alternatively, there may initially be a small gap between the retaining rim 54 and the upper surface of the shoulder 74. The gap may remain or be eliminated when, upon heat sterilization of the assembly 22, the cap 44 deforms. In the latter case, the rims 32, 54 abut or contact the lower surface and upper surface respectively of the annular shoulder 74. Thus, the crown 46 and the reseal housing 24, along with the annular shoulder 74 and the lip 84 of the reseal element, cooperate to provide a substantially permanent mechanical second means of securing the reseal element 72, which can be independent of the fit between the reseal element 72 and the open cylinder 30 and eliminates the need for separate fasteners, solvent bonding or swaging the reseal element 72 in place. In addition to positively retaining the reseal element 72 in place, the cap assembly 38 provides a removable cap 44 that seals the reseal element 72 from contamination until use. Despite the fact that the reseal element 72 is neither solvent bonded nor swaged into place, its securement is unaffected by component size, needle gauge, insertion force on the needle 18 or the removal of the cap 44. The reseal element 72 is automatically mechanically retained in place and constrained against movement both axially and radially primarily by the connection of the crown 46 and reseal housing 24.

With reference to FIGS. 1-3B, 9, and 10, an administrative port closure assembly 88 is shown as the second port closure assembly of the port closure system 10. The administrative port closure assembly 88 is adapted to provide piercing pin set 20 sterile access to the second fluid port 16. The administrative port closure assembly 88 is also adapted to be assembled and sterilized as a subassembly prior to association and use with the fluid container 12.

Figure 9:
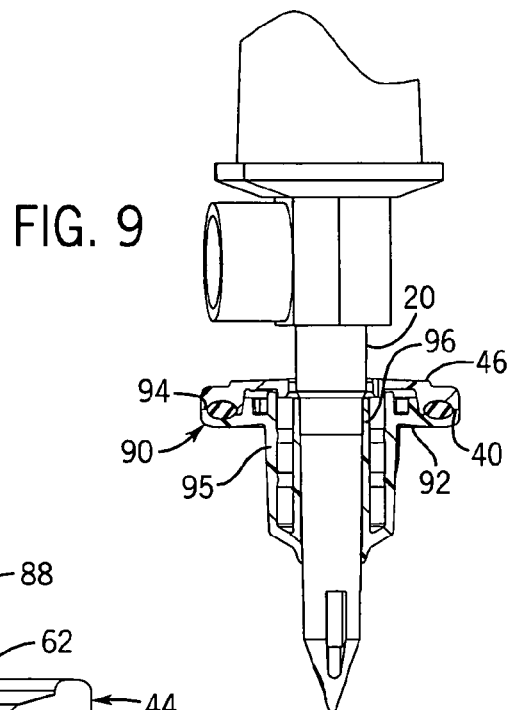
FIG. 9 is a sectional view of the administrative port closure assembly of the present invention in use with a piercing pin set.
Figure 10:
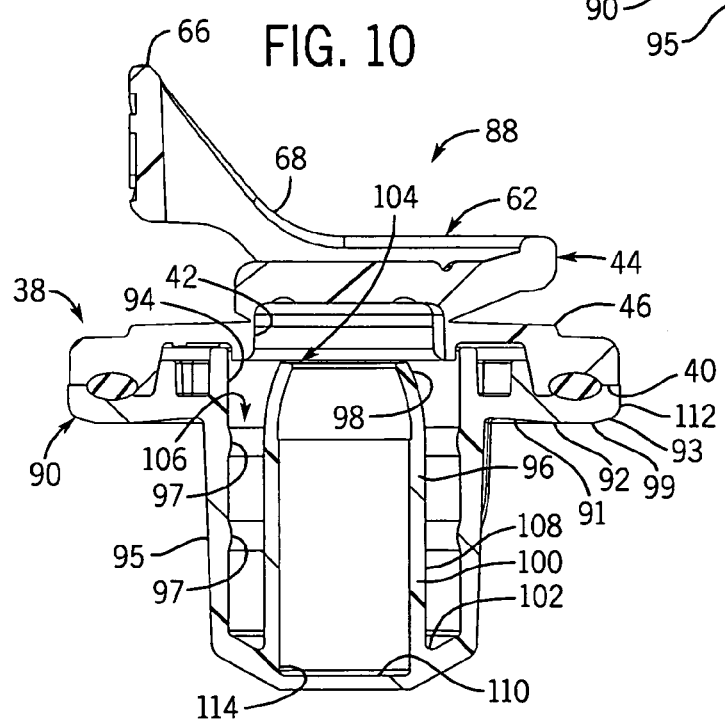
FIGS. 10 is a cross sectional view of one embodiment of the administrative port closure assembly of the present invention.

With reference to FIGS. 1, 9 and 10, the administrative port closure assembly 88 includes a second port housing 90 (hereinafter "administrative housing 90") adapted to seal closed the second fluid port 16 by attachment to the fill tube 15. A base surface 92 is adapted to be associated with the second fluid port 16 or fill tube 15 and an interior surface 94 is adapted to face outwardly from the second fluid port 16.

A seal ring 95 extends from the base surface 92 and is adapted to be sealably received within the second fluid port 16. The seal ring 95 has a stiff construction and large diameter of about ⅝" to provide improved user handling of administrative port closure assembly 88. An optional stiffening hoop or rib 97, more preferably a pair of spaced ribs 97, extends radially inwardly on the seal ring 95 to stiffen the seal ring and resist deformation during heat sealing to the port 16 and later autoclave heat sterilization.

A sleeve 96 extends from the interior surface 94 past the base surface 92 and within the seal ring 95. The sleeve 96 is recessed below sealed opening 42 of second cap assembly 38 connected to the administrative housing 90. This recess protects the sleeve from inadvertent contamination of interior surface 94 when the administrative port closure assembly 88 is opened. The sleeve 96 has an upper portion 98 and a lower portion 100. The upper portion 98 is adjacent the interior surface 94 and has an opening 104 with a lesser diameter than the lower portion 100. The diameter difference between the upper and lower portions 98 and 100 allows the sleeve 96 to receive and sealably associate with differently sized piercing pin sets 20, and to accommodate diameter variation among various piercing pin sets 20.

In the embodiment disclosed in FIG. 10, the upper portion 98 has a substantially uniform wall thickness and is tapered inwardly into a bullet nose configuration where the exterior surface is convex and the interior surface is concave. The taper can be formed by any number of well-known manufacturing techniques, including but not limited to cutting, rolling (with or without heat) and swaging. The taper of the upper portion 98 is preferably curvilinear, but linear taper can also be used. During use the user's fingers are within ¼" of the sleeve 96, allowing the user to easily control the position of the sleeve 96 with respect to piercing pin sets 20.

The sleeve 96 and the seal ring 95 are connected at a flexible annular junction 102 at a base 114 for the sleeve to form a unitary body. The flexible junction 102 allows for some minor displacement of the sleeve 96 with respect to the rigid seal ring 95 during use.

An air-filled moat 106 is positioned between the seal ring 95 and the sleeve 96 on the base surface 92. The moat 106 allows the seal ring 95 to contract and expand as needed based on internal pressure of the container 12 during the heat sterilization cycle. Thus, the moat 106 protects the sleeve 96 from significant permanent deformation that could lead to leaks or unacceptable insertion or withdrawal force requirements. The connection between the seal ring 95 and sleeve 96 provides a clamping or sealing force on piercing pin set 20 (not shown) during pin insertion and withdrawal. In addition to being physically separated from the sealing ring 95 except at the base 114, the sleeve 96 is protected by the seal ring 95 and moat 106 from potential distortion during autoclaving, since the moat 106 reduces outside pressure against sleeve 96 during autoclaving.

An administrative diaphragm 110 is connected to the sleeve 96 to seal the sleeve 96 closed to fluid flow. The administrative diaphragm 110 is opened to fluid flow once pierced by piercing pin set 20.

An administrative flange 112 extends generally radially from the seal ring 95, and thus from the sleeve 96. The administrative flange 112 around the sleeve 96 creates an effective target area for the user to apply the piercing pin set 20 toward and protects the user from accidental pricks.

A second cap assembly 38 is connected to the administrative housing 90 to form the administrative port closure assembly 88. The under shell 40 is shaped to mate with the interior surface 94 of the administrative housing 90. Once mated, the cap assembly 38 seals the interior surface 94 from potential contamination. The removable cap 44 provides access to the sealed opening 42 and thus the interior surface 94. Once the removable cap 44 is detached, the administrative port closure assembly 88 need not be re-sterilized, as the cap assembly 38 operates as a sterile barrier to shield the interior surface 94 from potential contamination.

With reference to FIG. 1, during manufacture of the port system 10, port housings 24/90, cap assembly 38 and reseal element 72 are mold formed. The additive port closure assembly 22 is formed by positioning reseal element 72 between the cap assembly 38 to the port housing 24, and permanently connecting the cap assembly 38 to the port housing 24. The administrative port closure assembly 88 is formed by connecting the cap assembly 38 to the port housing 90. Port closure assemblies 22/88 are connected together by ultrasonically welding or radiant thermofusion welding the cap assembly 38 to the port housing 24/90. Port closure assemblies 22/88 are sterilized by irradiation. The irradiated pre-sterilized port closure assemblies 22/88 form subassemblies that are subsequently associated with or attached to the fluid container 12. The fluid container 12 is sealed to the irradiated port closure assemblies 22/88 by conventional means, including but not limited to ultrasonically welding, radiant thermofusion welding, or hot tongue heat sealing. The associated port closure assemblies 22/88 and fluid container 12 are then terminally heat sterilized by autoclaving after filling.

Port closure assemblies 22/88 are formed of a polymer blend that does not degrade during the irradiation, sterilization, radiant thermofusion welding, and ultrasonic welding. The term "degrade" as used herein refers to degradation to such an extent that the material is no longer suitable for its intended purpose. The polymer blend also provides ultrasonic sealability, radiant thermofusion sealability, and prevents coring when the polymer is punctured. The term "coring" as used herein refers to the process of a polymer fragmenting upon piercing so as to result in the formation of loose polymer particulate. The ability of polymer blend to be sealed by ultrasonic bonding and/or radiant thermofusion eliminates the need for any solvent or swaged bonding; and also eliminates the need to provide additional frictional force fit components to hold the port closure system 10 together. Additionally, the polymer blend provides a balance between insertion and withdrawal forces for improved handling by users.

One example of such a polymer blend includes but is not limited to a blend of 70% commercially available Atofina Z9470 and 30% commercially available Basell KS359P. Other suitable polypropylene copolymers and polyethylene copolymer blend could also be used without departing from the present invention.

Materials are selected for the IV fluid container 12, fill tube 13, 15, port housings 24, 90, and cap assembly 38 to provide, in conjunction with their design, the required container and port system functionality. While the difference in function among these parts requires different physical properties that may be supplied by a variety of materials, the materials must be compatible on a molecular level to enable them to be joined together without adhesives.

The fill tube 13, 15 is formed of a material that is sealable to the inner sealant surface of the IV fluid container 12 and the port housings 24, 90. It must be able to be autoclaved without deformation that significantly affects its appearance or function of providing a channel between the container 12 and the ports 14, 16. For sealant surfaces of containers 12 and port housings 24, 90 that comprise polyolefins such as polypropylene homopolymers, polypropylene copolymers, or blends of polypropylene copolymers with materials providing elastomeric properties, the fill tube 13, 15 preferably comprises a polypropylene homopolymer or copolymer. A homopolymer provides better dimensional stability through autoclaving, while a copolymer provides better compatibility with an IV container 12 that has a copolymer sealant surface. For container sealant surfaces and port housings that comprise random polypropylene copolymers or blends of random polypropylene copolymers with materials providing elastomeric properties, the fill tube 13, 15 preferably comprises a random polypropylene copolymer with ethylene content from about 2% to about 6% and a melting point from about 129° C. to about 145° C. To reduce deformation with autoclaving at 125° C., the random polypropylene copolymer more preferably has an ethylene content of about 2% and a melting point of about 145° C. Specifically, a random polypropylene copolymer, Atofina 7825, has been found to produce the best results at autoclave temperatures up to about 125° C. with a container 12 with polypropylene copolymer sealant layer and port housings 24, 90 comprising a blend of polypropylene copolymers.

The administrative port housing 90 must be heat sealable to both the fill tube 13 and cap assembly 38, as well as be stable to gamma radiation from 18-45 kGy, more preferably from 18-32 kGy. The administrative port housing 90 must be autoclavable up to about 125° C. without deformation that significantly affects its function of being able to accept and retain a piercing pin 20 with acceptable forces. Preferably the material selected for the administrative port housing 90 has a high melt temperature and good elastomeric properties. A material blend is preferred to provide properties not available from individual materials. A polypropylene based material is preferred primarily for its chemical compatibility with the polypropylene fill tube 13. Further material selection is dependent on radiation stability, autoclave temperature, and the range of piercing pin diameters to be used. Generally, polypropylenes with higher melting points such as homopolymers or copolymers with low ethylene content, for example Atofina 7825 that has 2% ethylene content, withstand autoclaving with less deformation. However, they have relatively high moduli, which increases piercing pin insertion force and limits the range of piercing pin diameters that may be used. They are also less stable to gamma radiation unless purposely stabilized with additives. While their performance may be improved by blending them with lower moduli, radiation stable polyolefins, it is preferable to use a high ethylene content (about 6% or greater) random copolymer as the base material. The high ethylene content improves radiation stability and lowers the modulus while maintaining acceptable resistance to autoclave deformation. It also reduces the concentration of the softening material required. Such softening material often has a lower melting point or is tacky and difficult to injection mold. Preferably a high ethylene content random polypropylene copolymer, such as Atofina Z9470, is used for the base material.

While an unmodified high ethylene content random polypropylene copolymer may provide acceptable performance with a single piercing pin diameter, it is preferable to soften the material with polypolyolefin copolymers such as thermoplastic polypolyolefin elastomers (TPEs) to broaden the range of acceptable piercing pin diameters and improve radiation stability. Acceptable performance also may be obtained with low ethylene content polypropylene random copolymer base materials with an appropriate selection of TPE and blend ratio. Similar to polypropylene copolymers, softer TPEs generally have lower melting points. Ethylene-hexene and ethylene-octene copolymer flexomers have very low moduli and melting points (72° C. and 55° C., respectively) substantially below the autoclave temperature of 125° C. However, when blended with a low ethylene content random copolymer at a ratio of 70% polypropylene copolymer/30% flexomer, they provide adequate softening and autoclave dimensional stability. An ethylene-octene flexomer, such as Dow Affinity EG8100, is preferred to reduce piercing pin insertion force. Polypropylene random copolymers with ethylene-propylene rubbers copolymerized in the copolymer matrix, such as Basell's Adflex materials, provide less softening than flexomers but have higher melt temperatures (approximately 144° C.). They are highly suitable for softening a high ethylene content random polypropylene copolymer base material, such as Atofina Z9470, because they reduce stiffness without reducing autoclave dimensional stability. Basell Adflex KS359P is one material that has been found to provide effective softening and radiation stability. Blends made from 40% Z9470/60% KS359P to 70% Z9470/30% KS359P may be used, with blends of about 70% Z9470/30% KS359P being more preferred.

The port cap assembly 38 must be sealable to both the administrative and additive port housings 90, 24 and stable to gamma radiation from 18-45 kGy, more preferably from 18-32 kGy. It must be autoclavable up to about 125° C. without deformation that significantly affects its function of maintaining sterility and being opened with an acceptable pull force. Key to an acceptable opening performance is developing an appropriate combination of material stiffness and tear detail thickness. The pull ring 68 or pull element 62 may snap off prior to opening the cap 44 with an excessively stiff material or thick tear detail. The pull ring 68 may stretch without opening the cap 44 or the cap 44 may deform during autoclaving with a material that is too soft. Materials that minimally provide the required properties are high ethylene content polypropylene copolymers such as Atofina Z9470 and random heterophasic polypropylenes such as Borealis Bosrsoft SD233CF. However, it is preferred to lower the opening force by using a TPE modifier. To maximize sealability to the administrative port housing 90, it also is preferred that the same materials be used in the same or similar ratio as used in the port housing 90. Basell Adflex KS359P again is highly suitable in that it provides softening without a loss in autoclave dimensional stability. A range of 100% Z9470/0% KS359P to 70% Z9470/30% KS359P is acceptable, with 70% Z9470/30% KS359P being more preferred.

Similar to the administrative port housing 90, the additive port housing 24 must be sealable to both the fill tube 13 and cap assembly 38 and stable to gamma radiation from 18-45 kGy, more preferably from 18-32 kGy. It must be autoclavable up to about 125° C. without deformation that significantly affects its function of being able to be pierced by a needle 18 without coring. To resist coring, it is preferred that the selected material has elastomeric properties. Polypropylene random copolymers with ethylene-propylene rubbers copolymers copolymerized in the copolymer matrix, such as Basell Adflex materials, are elastomeric and sealable to the 70% Z9470/30% KS359P port cap. Adflex KS359P is preferred among the Adflex materials for coring performance because it is the most elastomeric in the current Adflex product line. To improve seal strength by maximizing chemical compatibility and to improve ejection during injection molding, it is preferred to use the same materials in the same 70%/30% blend ratio as the cap assembly 38. To maximize coring performance at the intended port diaphragm 34 thickness of 18 mils, a range of 40% Z9470/60% KS359P to 0% Z9470/100% KS359P is preferred. To optimize injection molding, sealing, and coring performance, a 40% Z9470/60% KS359P blend is more preferred. The range may be adjusted depending upon diaphragm thickness, with thicker diaphragms generally requiring a higher elastomeric concentration. The blend of resins used for the various parts to be sonic or heat welded must provide melting points that are not so dissimilar as to prevent proper sealing security or reliability.

Figure 11:
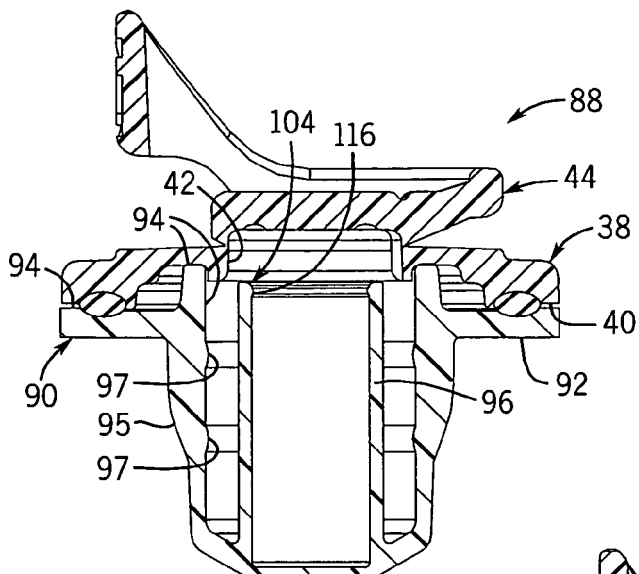
FIGS. 11-15 are cross sectional views of additional administrative port closure assembly embodiments.

With reference to FIG. 11, a still further embodiment of administrative port closure assembly 88 includes many of the same features as the embodiment of FIG. 10, but instead of the tapered sleeve end further includes a small wiper 116 adjacent the aperture 104 of sleeve 96 to seal against piercing pin set 20 (not shown). The sealing of the wiper 116 against the piercing pin set 20 (not shown) reduces the chance for fluid to leak out during activation. It will be understood to those skilled in the art that various methods including but not limited to swaging at the aperture 104 could be used to form the wiper 116. The wiper 116 could also be combined with a tapered sleeve end of FIG. 10.

Figure 12:
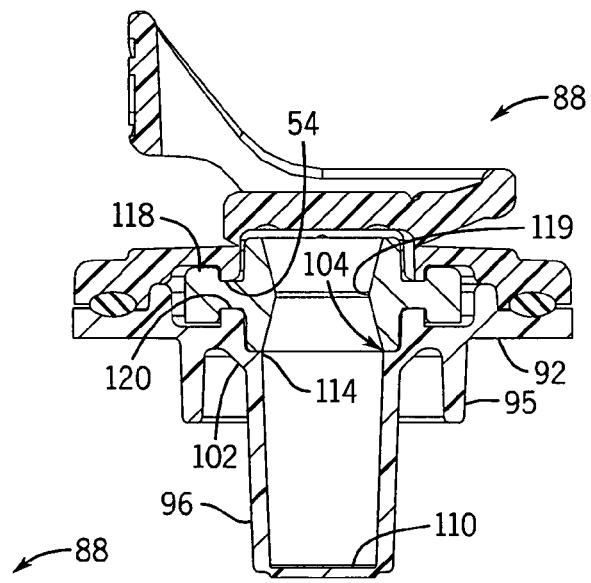

With reference to FIG. 12, a still further embodiment of administrative port closure assembly 88 includes some of the features of the embodiment of FIGS. 9-11 but further includes a pre-pierced administrative seal washer 118 having a wiping diameter 119, retained, secured, held, or more particularly (especially once heat sterilized) clamped in place between the retaining rim 54 and an administrative rim 120 extending from shoulder 102. The administrative seal washer 118 seals against piercing pin set 20 (not shown). To moderate and balance the forces required to insert and withdraw the pin set 20, the wiping diameter 119 can be centrally located and the pre-pierced diameter can be gradually increased as distance from the wiping diameter increases.

Figure 13:
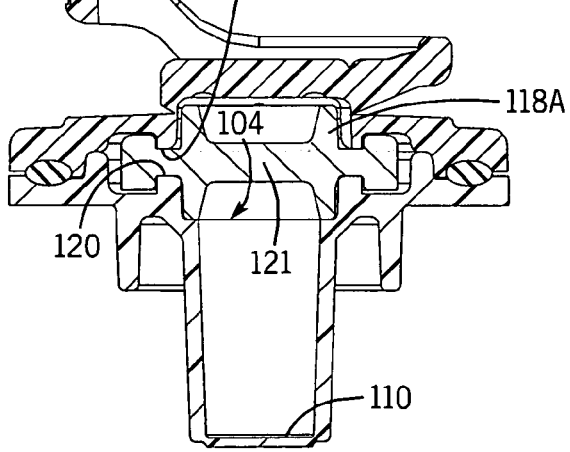

With reference to FIG. 13, a still further embodiment of administrative port closure assembly 88 includes some of the features of the embodiment of FIG. 12 but includes an administrative reseal 118A similar to the reseal element 72 of the additive port closure assembly 22, retained, secured, held, or more particularly clamped in place between the retaining rim 54 and an administrative rim 120 extending from shoulder 102. Similar to the reseal element in the additive port closure assembly 22, the administrative reseal 118A is clamped by the rims 54 and 120, especially once the assembly 88 is heat sterilized. The administrative reseal 118A seals against piercing pin set 20 (not shown). Since the reseal element 118A completely seals the opening 104 of the sleeve 96, the diaphragm 110 is optionally excludable in this embodiment. The central diaphragm 121 of the reseal 118A is relatively thick (greater than 0.050 inch or 1.27 mm) in the embodiment of FIG. 13. A still further embodiment can combine the features of FIGS. 12 and 13 so that the reseal element 118A includes a thin (0.010-0.050 inch or 0.254-1.27 mm) central diaphragm 121 rather than a pre-pierced opening or wiping diameter 119 or the thick central diaphragm 121 of at least 0.050 inch or 1.27 mm shown in FIG. 13. This thin diaphragm configuration is advantageous in that it makes the reseal element easier to mold and does not leave flash in undesirable areas.

Figure 14:
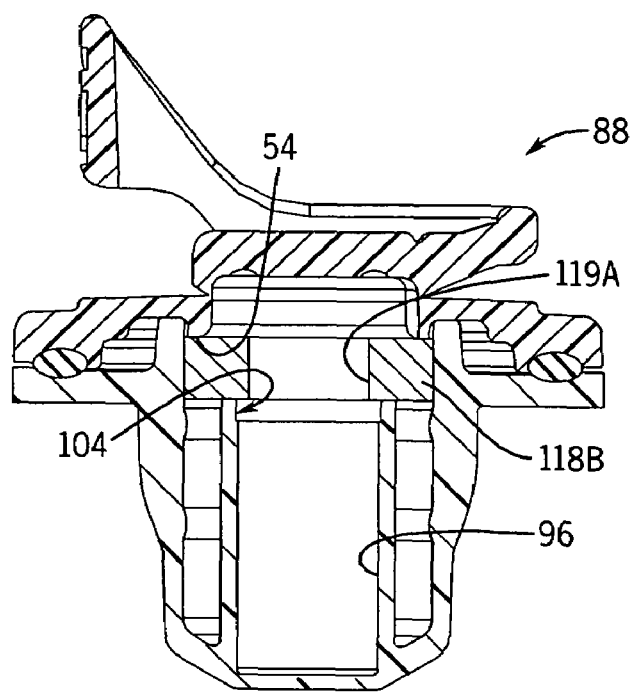

With reference to FIG. 14, a still further embodiment of administrative port closure assembly 88 includes some of the same features as the embodiment of FIG. 10, but further includes an either injection molded or extruded administrative sealing washer 118B with an inner diameter 119A that seals against piercing pin set 20 (not shown). The sealing washer 118B is retained, secured, held, or more particularly (especially once the assembly is heat sterilized) clamped in place between the retaining rim 54 and the sleeve 96.

Figure 15:
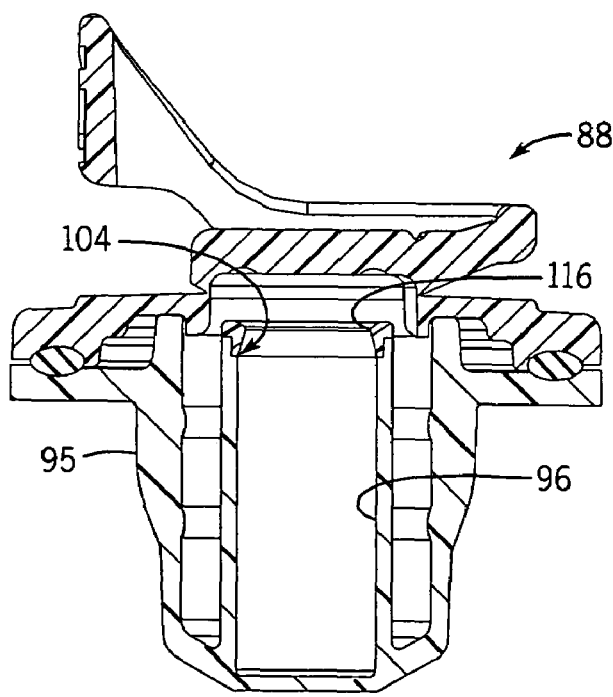

With reference to FIG. 15, a still further embodiment of administrative port closure assembly 88 includes a small wiper 116 similar to the embodiment of FIG. 11, but the wiper 116 and sleeve 96 form a unitary body that is molded through co-injection molding so that small wiper 116 has a different polymer content than sleeve 96. The wiper 116 is formed of isoprene and will generate holding forces during activation with the piercing pin set 20 (not shown).

Figure 16:
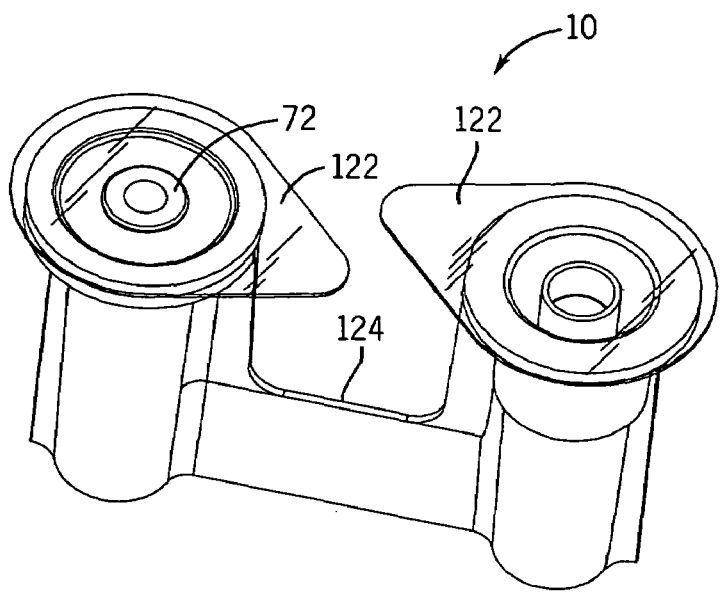
FIGS. 16-17 are perspective views of additional port closure system embodiments.

With reference to FIG. 16, another embodiment of port closure system 10 replaces cap assemblies 38 with cover foils 122. The cover foils 122 are made of pealable film stock. In this embodiment reseal element 72 is swaged in place. A body portion 124 joins the administrative port assembly 88 and additive port assembly 22.

Figure 17:
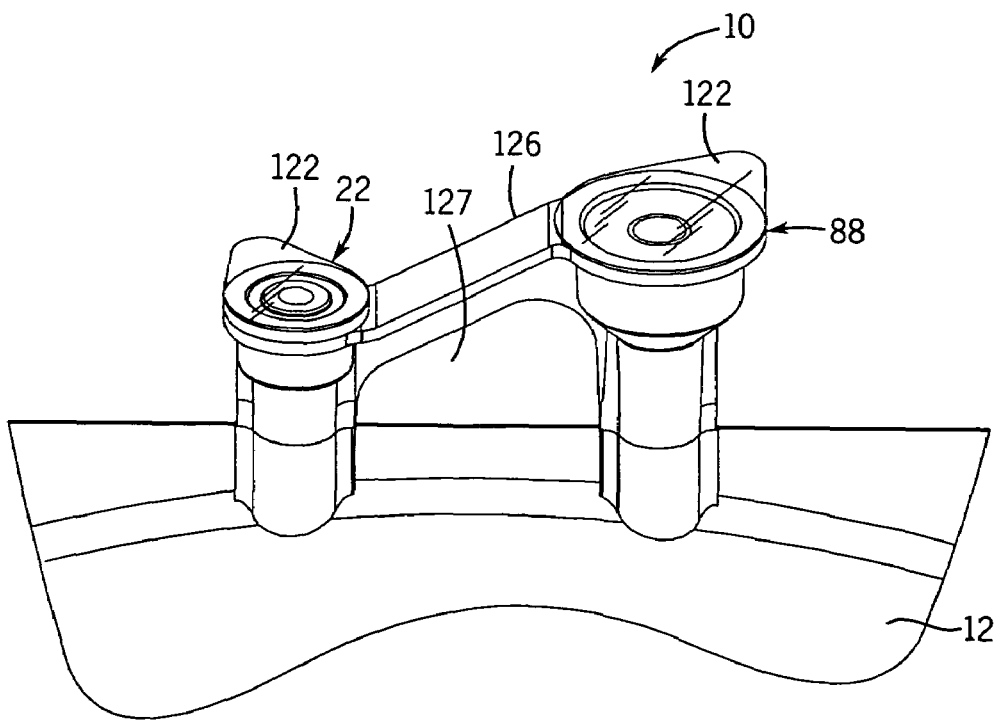

With reference to FIG. 17, a further embodiment of port closure system 10 includes the same features as the embodiment of FIG. 16, and further includes a handle element 126 joining the port assemblies 22, 88 so as to define a space 127 between the handle portion 126 and the fluid container 12, thus permitting a user to loop fingers around handle portion 126. Additionally, additive port assembly 22 is sized smaller than administrative port assembly 88 and is positioned lower with respect to the administrative port assembly 88, to further distinguish the additive port assembly 22 from the administrative port assembly 88.

Figure 18:
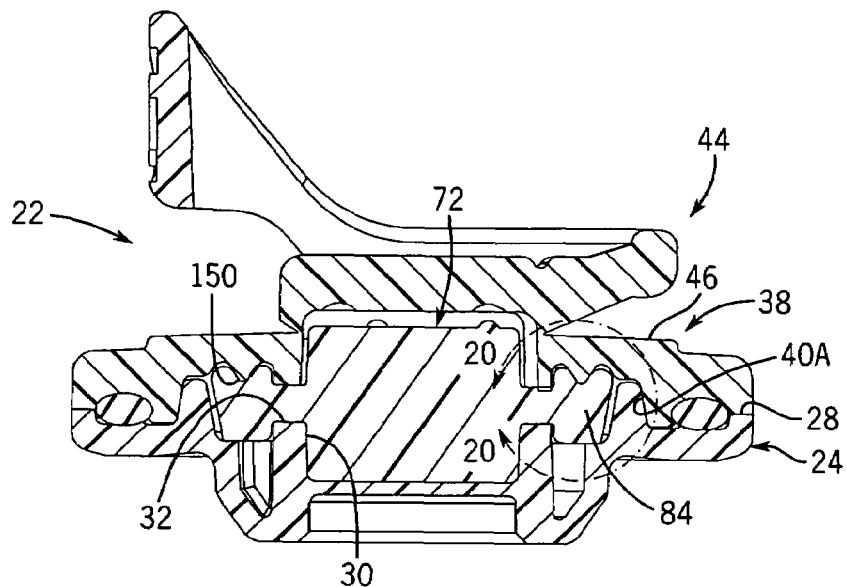
FIG. 18 is a cross sectional view similar to FIG. 4 of an alternative embodiment of the additive port closure assembly.
Figure 19:
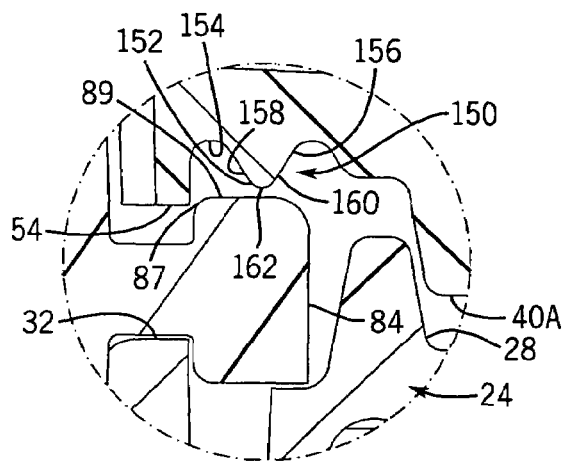
FIG. 19 is an enlarged partial cross sectional view of a portion of the additive port closure assembly from FIG. 18 prior to the cap assembly being joined to the reseal housing.
Figure 20:
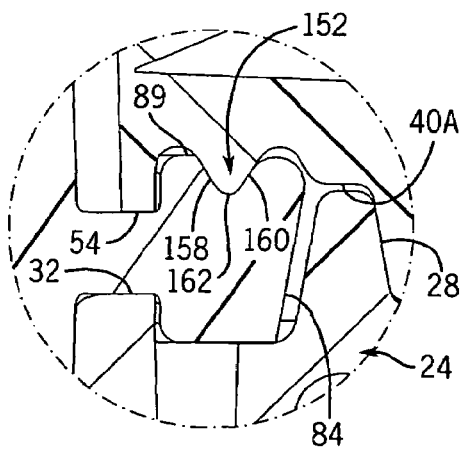
FIG. 20 is an enlarged partial cross sectional view of the additive port closure assembly and shows the area encircled by the line 20-20 in FIG. 18.
Figure 21:
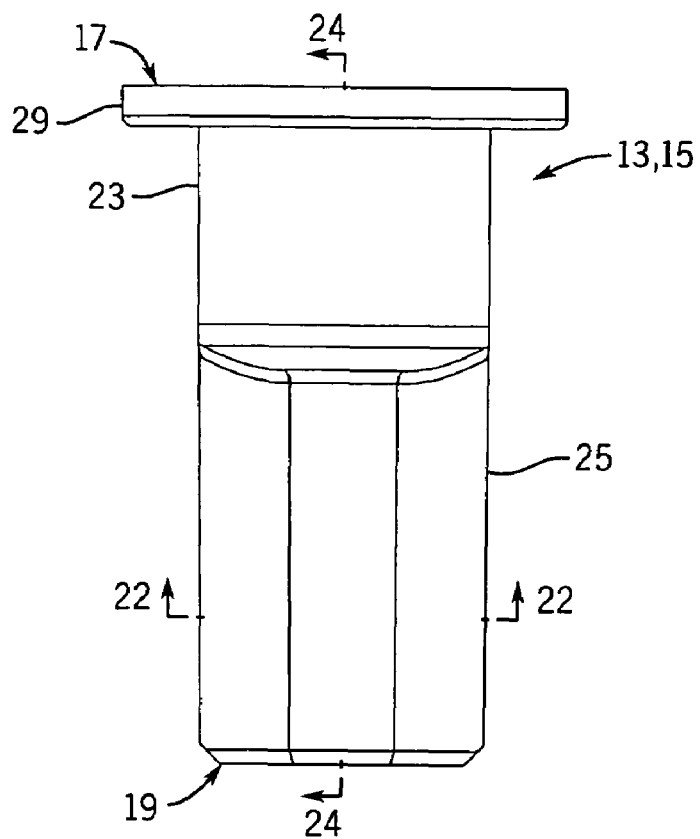
FIG. 21 is a front plan view of a fill tube port according to one embodiment of the invention.
Figure 22:
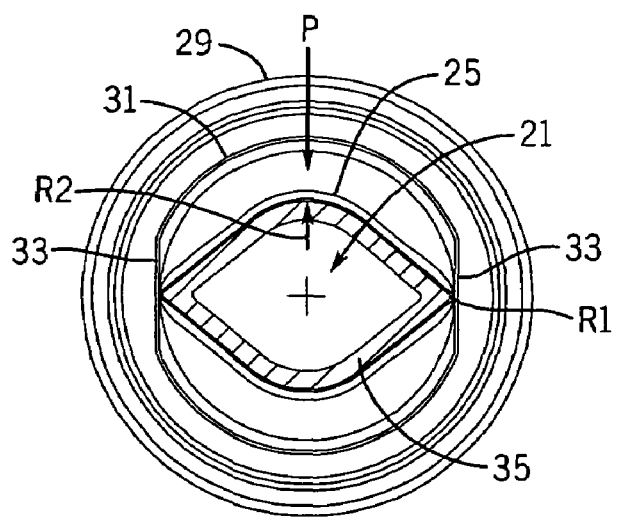
FIG. 22 is a sectional view of the fill tube taken along line 22-22 in FIG. 21 and shows the non-circular transverse cross-section of the lower portion of the fill tube.
Figure 23:
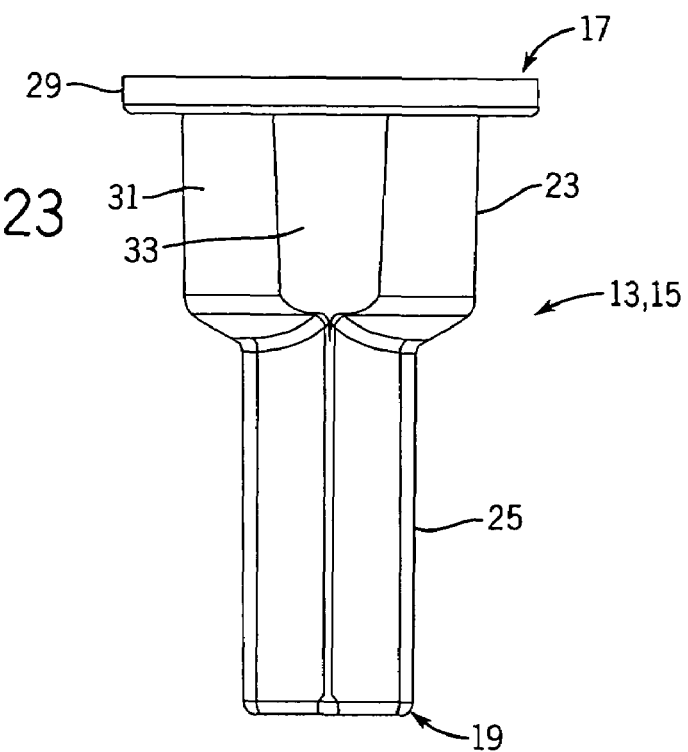
FIG. 23 is a side elevation view of the fill tube of FIG. 21.
Figure 24:
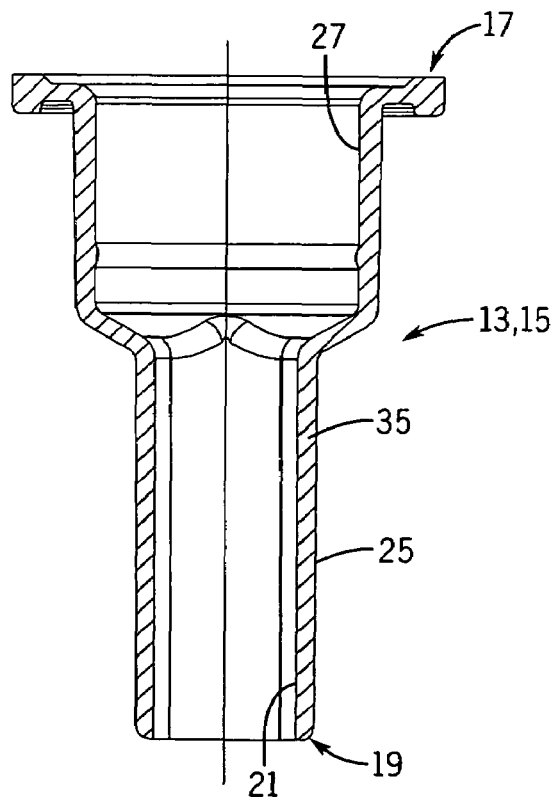
FIG. 24 is a longitudinal sectional view of the fill tube taken along line 22-22 in FIG. 21.

With reference to FIGS. 18-20, a further embodiment of the additive port closure assembly 22 includes a reseal housing 24 and reseal element 72 as described above. However, the under shell 40A of the cap assembly 38 differs in some respects from the under shell 40 previously described. The under shell 40A of the crown 46 includes at least one sealing element 150 for engaging the lip 84 of the reseal element 72. Preferably the sealing element 150 engages the top surface 89 of the lip 84.

Although one skilled in the art will appreciate from this disclosure that the sealing element 150 can take various forms and shapes, in the embodiment shown, the sealing element 150 includes at least one protrusion 152 that extends downwardly from the under shell 40A and defines 154, 156 troughs on either side thereof. The protrusion 152 can be generally V-shaped in cross section and have angled sides 158, 160 that converge to form a blunt, rounded tip 162. Preferably the protrusion 152 extends around the under shell 40A in a circular pattern. The circular pattern can be broken to form circumferentially spaced protrusions or can be unbroken to form a continuous annular protrusion. Alternatively, the sealing element 150 can include a plurality of concentrically arranged protrusions 152.

As best seen in FIG. 20, the sealing element 150 engages the lip 84 between the under shell 40A and the interior or inner surface 28 when the under shell 40A of the crown 46 is connected, attached or joined to the inner surface 28 of the reseal housing 24 as described above. The tip 162 and angled sides 158, 160 of the protrusion 152 or sealing element 150 contact and sealingly engage the top surface 89 of the lip 84. The reseal element 72 resiliently deforms around the protrusion 152. The engagement of the protrusion 152 with the resilient reseal element 72 provides a clamping force on the lip 84, clamping it between the protrusion 152 on the under shell 40A and the inner surface 28 of the reseal housing 24. When the sealing element 150 includes one or more protrusions 152 arranged a sufficiently closed annular pattern, this arrangement provides an effective seal against liquids, vapors and gases that might otherwise pass around the reseal element 72. The invention assists in preventing contamination from reaching the inner surface 28 when the user removes the detachable cap 44. Undesirable ingress and egress of liquids, vapors or gases is prevented during the sterilization of the port closure assembly 22 or the fluid container 12 to which the port closure assembly is attached. This embodiment of the invention provides the additional benefit of further restraining the reseal element 72 against movement that might otherwise occur during insertion or withdrawal of a needle 18 or similar piercing member.

One skilled in the art will appreciate that the principles of FIGS. 18-20 can be applied alone or in combination with other features disclosed herein. By way of example and not limitation, the principles are applicable to administrative port closure assemblies that utilize a reseal element, such as the embodiment of FIG. 13.

Figure 4:
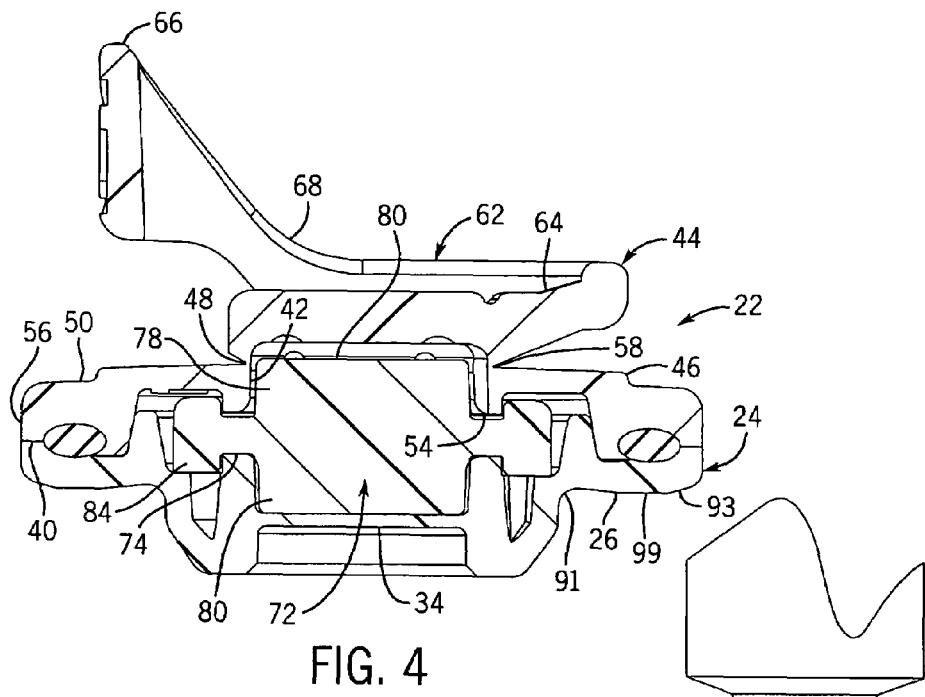
FIG. 4 is a sectional view of the additive port closure assembly of the present invention.
Figure 5:
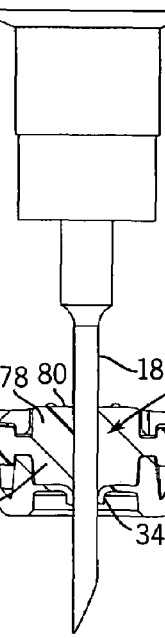
FIG. 5 is a sectional view of the additive port closure assembly of the present invention in use with a needle.

With reference to FIGS. 4 and 10, the port housings 24, 90, which are sealingly attached to the cap assembly 38 and fluidly seal the ports 14, 16 respectively in one embodiment by attachment to the flange 29 of the fill tube 13, 15, each can include additional beneficial features. The port housing 24, 90 has an undercut or annular recess 91 formed on an annular portion of the base face 26 or base surface 92 respectively. The annular portion of the base face 26 or base surface 92 also has a chamfered outer edge 93 and a contact ring 99 located between the annular recess 91 and the chamfered outer edge 93. In one embodiment the contact ring 99 is smooth, planar and substantially horizontal. The recessed, chamfered, and ringed configuration provides a good contact surface at the ring 99 for attaching the port housing 24, 90 to the cap assembly 38 by ultrasonic welding, and later for attaching the port closure system or assemblies 22, 88 to the fill tubes 13, 15 at the flange 29 by hot tongue welding or other means. The annular recess 91 and the chamfered outer edge 93 also help eliminate or redirect into harmless areas any flash from molding of the port housing 24, 90 or hot tongue welding.

The construction and fabrication of the flexible container 12 or bag of the present invention will now be described in greater detail. As mentioned earlier, the container 12 includes a container body 1. As best seen in view of FIGS. 27, in one embodiment, the container body 1 has front and back portions 3A, 3B, which can be separate double wound sheets of flexible multiple layer polyolefin film sealed together by heat sealing or other means along an outer peripheral seam 5. In another embodiment, the front and back portions 3A, 3B could be formed by folding a single sheet of film over upon itself.

In one embodiment, a conventional non-PVC polypolyolefin film commercially available from Sealed Air Corporation under the trade designation CRYOVAC M312 is used in the container 12 with the port closure system of the present invention. This material has been found to exhibit excellent compatibility with the non-PVC materials preferred for the fill tubes 13, 15 and port closure systems. As best seen in FIG. 28, each sheet of the CRYOVAC M312 material defining the front and back portion 3A, 3B has five layers. The first layer L1, which is also referred to herein as a sealant layer or the inner layer, is a polypropylene layer that is adapted to be heat sealed, welded or fused to itself using conventional attachment techniques, including but not limited to heat welding. The second layer L2, which is also referred to as a base, outer or release layer, is a polyester layer adapted to contact and release from the heat sealing tool. A polyethylene middle barrier layer L3 is disposed between the inner and outer layers L1, L2. An inner tying layer L4 is located between the middle layer L3 and the inner layer L1. An outer tying layer L5 is located between the middle layer L3 and the outer layer L2. The tying layers L4, L5 attach the first layer L1 and the second layer L2 respectively to the third or middle layer L3.

Containers 12 filled with approximately 500 ml or 1000 ml of medical fluids, with the port closure system 10 described herein and a container wall 3 of CRYOVAC M312 having an overall thickness of about 8 mils have been shown to provide a shelf life up to or greater than 24 months and a moisture vapor transmission rate (MVTR) of less than about 0.060 g/100 in$^2$-day. On-going tests indicate that the shelf life might be extendable up to 36 months. Containers 12 of 500 ml or larger made of this film and the port closure system disclosed herein do not require supplemental moisture barriers or overwraps on the individual containers to achieve these results. As shown in Table 2 below, these containers 12 compare favorably in terms of MVTR to conventional containers constructed of monolayer PVC film.

TABLE 2

Direct WVTR Rate Comparison Between PVC and Polyolefin Container

| Material | Test Result (Tested at 25 Deg. C. and 40% RH) |
| --- | --- |
| PVC without overwrap | 0.24 g/100 sq. in. - day |
| Polyolefin (CRYOVAC M312) | 0.053 g/100 sq. in. - day |

The polyolefin container 12 can be fabricated by taking double wound film from either a blown film or cast film process and feeding it into a bag fabricator as a continuous web. The containers 12 or bags are normally made side by side on the web of film with the fill ports 13, 15 protruding from one edge of the web.

The film first has label copy applied to it via one or more conventional processes. Hot stamping, lithography, thermal transfer printing or a combination of these can be employed to place any necessary label information onto the container.

Figure 26A:
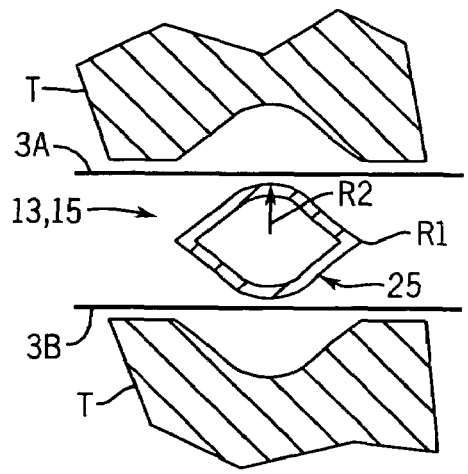
FIG. 26A-26C is a series of sectional views showing the tooling, film and the lower portion of the fill tube of FIG. 21 before and during attachment to the body of the container according to the present invention.
Figure 26B:
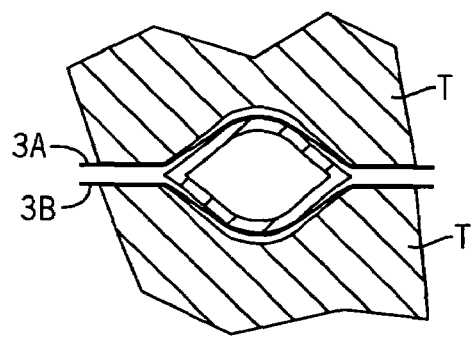
Figure 26C:
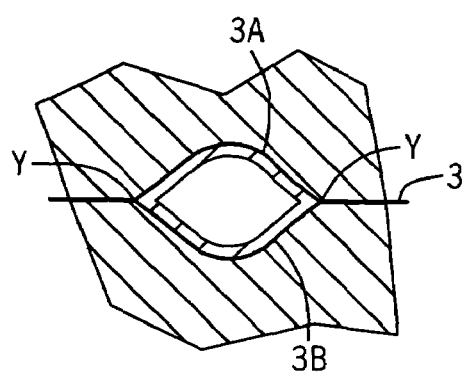

The film is then opened and fill tubes 13, 15 are place between the two film sheets or front and back portions 3A, 3B as illustrated in FIGS. 26A. The fill tubes 13, 15 are then heat sealed to the two sheets of film or the front and back portion 3A, 3B by a tool T.

The film is then passed through a perimeter sealing press that further seals the fill tubes 13, 15 between the sheets 3A, 3B, creates the perimeter or outer peripheral seal 5, and separates the containers.

The individual bags are then turned so that the fill tubes 13, 15 extend vertically. Then the fluid reservoir 2 of the container body 1 is filled with a predetermined volume of medical solution through one or more of the fill tubes 13, 15. Of course, only one fill tube may be sufficient for some applications.

The top of the fill tube flanges 29 is then radiantly heated to accept the port assemblies 22, 88. Simultaneously, the base face or base surface 26, 92 of the port housings 24, 90 is radiantly heated. The heat source is then removed and the port assemblies 22, 88 and the fill tubes 13, 15 are pressed together under controlled pressure and time conditions.

Another way of bonding the port assemblies 22, 88 to the fill tubes 13, 15 is via ultrasonic welding. In this process the port assemblies 22, 88 and the fill tubes 13, 15 are pressed together while ultrasonic energy is passed through them. Once the ultrasonic energy has been applied, the parts continue to be held tightly together until the materials have resolidified.

The filled containers 12 are placed into an autoclave for steam heat sterilization to assure that the final product is sterile. The container contents are steam sterilized using a cycle of 121+4/−0 degrees C. with a peak dwell of 15 minutes for the coldest container.

A plurality of the individual filled containers 12 are then placed in a shipping carton, stored, eventually shipped to a user.

One skilled in the art will appreciate that the present invention can be applied to flexible containers for enteral nutritional or other medical fluids as well.

From the foregoing, it can be seen that the present invention accomplishes at least all of the stated objectives. The invention provides a port closure system that reduces the possibilities of contamination during storage and use, improves the ease of handling when fluids are to be withdrawn or introduced, and increases the ease and efficiency of manufacture. The invention provides a container that is free of PVC and DEHP. The container has a low MVTR, which enables greater manufacturing tolerances around the target fill volume.

What is claimed is:

1. A flexible fluid container comprising:
a flexible container body having a fluid reservoir formed therein surrounded by a container wall, the container body includes at least one port therein comprising an elongated fill tube having a proximal end, a distal end, and a fluid passage extending from the proximal end to the distal end; the distal end extending from the container body and the proximal end being attached to the container body such that the fluid passage is in fluid communication with the fluid reservoir; the fill tube including a non-circular lower portion adjacent to the proximal end, the non-circular lower portion defining an outer perimeter surface adjacent to the proximal end of the fill tube;
the container wall having opposing interior surfaces that are brought into surface contact with the outer perimeter surface of non-circular lower portion and directly sealed thereto so as to form a fluid tight seal around the lower portion of the fill tube; and a port closure system for sealing the at least one port; and
wherein the fill tube includes an upper portion that is generally cylindrical and includes an annular flange thereon extending outward radially and an outer surface disposed below the flange, the outer surface including a pair of opposing flat bottomed notches formed thereon extending longitudinally along the fill tube.

2. A container according to claim 1, wherein the fill tube has a longitudinal axis, and wherein the non-circular lower portion has a transverse cross-section shape that is selected from a group of shapes consisting of oval, semi-oval, elliptical, semi-elliptical, rhomboidal and semi-rhomboidal, and has a major axis and a minor axis transverse to the major axis, both the major axis and the minor axis are perpendicular to the longitudinal axis of the fill tube, and wherein the major axis has a greater length than the minor axis.

3. A container according to claim 2, wherein the notches on the upper portion of the fill tube define planar, flat-bottomed notches that are perpendicular to the major axis of the lower portion of the fill tube.

4. A container according to claim 2, wherein the major axis terminates at opposite ends that define a width of the lower portion of the fill tube and the minor axis terminates at opposite ends that define a depth of the lower portion of the fill tube, the width of the lower portion of the fill tube being greater than the depth of the lower portion of the fill tube.

5. A container according to claim 4, wherein the lower portion of the fill tube has an outside radius formed on the opposite ends of the major axis.

6. A container according to claim 5, wherein the outside radius formed on the opposite ends of the major axis is a 0.005 to 0.015 inch radius.

7. A container according to claim 4, wherein the lower portion of the fill tube has an outside radius formed on at least one of the opposite ends of the minor axis.

8. A container according to claim 7, wherein the outside radius formed on at least one of the opposite ends of the minor axis is a 0.125 to 0.250 inch radius.

9. A container according to claim 2, wherein the container wall has a back portion and a front portion superimposed over and sealingly joined along an outer peripheral seam to the back portion in a contact plane to define the fluid reservoir, the lower portion of the fill tube being inserted between the front portion and the back portion of the container wall such that the major axis of the lower portion of the fill tube resides in the contact plane and the front portion and the back portion of the container wall are sealingly joined to the lower portion of the fill tube.

10. A container according to claim 9, wherein the back portion and the front portion are each a sheet of multiple layer flexible polyolefin film selected such that the container has a moisture vapor transmission rate of less than 0.060 g/100 in$^2$-day.

11. A container according to claim 10, wherein the at least one port comprises a pair of ports each equipped with a fill tube and a port closure system, the lower portion of each of the fill tubes being attached to the container body such that the fill tubes are independently movable and spaced apart sufficiently for a user to insert at least one finger therebetween.

12. A container according to claim 10, wherein the multiple layer flexible polyolefin film includes a barrier layer disposed between the inner layer and the outer layer, an inner tying layer located between the barrier layer and the inner layer, and an outer tying layer located between the barrier layer and the outer layer, the barrier including one side attached to the inner layer by an inner tying layer and an opposite side attached to the outer layer by an outer tying layer.

13. A container according to claim 1, wherein the fill tube is about one to two inches long.

14. A container according to claim 13, wherein the fill tube is about 1.4 - 1.8 inches long.

15. A container according to claim 1, wherein the fill tube is defined by a fill tube wall that has sufficient thickness and rigidity to prevent an 18 gauge needle from being pushed through the fill tube wall on a path perpendicular to the fill tube wall when up to 6 lbs of force is applied.

16. A container according to claim 15, wherein the fill tube comprises a random polypropylene copolymer with ethylene content from about 2% to about 6% and a melting point from about 129° C. to about 145° C.

17. A container according to claim 16, wherein the fill tube wall has a substantially uniform thickness of between about 0.9 and 1.5 mm.

18. A container according to claim 1, wherein the container body, the fill tube and the port closure system are free of PVC and DEHP.

* * * * *